US008258347B2

(12) United States Patent
Popik et al.

(10) Patent No.: US 8,258,347 B2
(45) Date of Patent: Sep. 4, 2012

(54) CYCLOPROPENONES AND THE PHOTOCHEMICAL GENERATION OF CYCLIC ALKYNES THEREFROM

(75) Inventors: Vladimir V. Popik, Watkinsville, GA (US); Andrei A. Poloukhtine, Scottsdale, AZ (US); Geert-Jan Boons, Athens, GA (US); Margaretha Wolfert, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 97 days.

(21) Appl. No.: 12/708,617

(22) Filed: Feb. 19, 2010

(65) Prior Publication Data
US 2010/0210854 A1   Aug. 19, 2010

Related U.S. Application Data

(60) Provisional application No. 61/238,835, filed on Sep. 1, 2009, provisional application No. 61/153,762, filed on Feb. 19, 2009.

(51) Int. Cl.
*C07C 49/00* (2006.01)
*C07C 49/04* (2006.01)
(52) U.S. Cl. .......................... 568/326; 568/609; 568/808
(58) Field of Classification Search .................. 568/326, 568/609, 808
See application file for complete search history.

(56) References Cited

FOREIGN PATENT DOCUMENTS
WO   WO 2009/067663 A1   5/2009

OTHER PUBLICATIONS

Eischer, et al., Tet. Lett., 1984, vol. 25(40), pp. 4495-4498.*
Aamer et al., "RAFT Polymerization of a Novel Activated Ester Monomer and Conversion to a Terpyridine-Containing Homopolymer," *J. Polym. Sci., Part A: Polym. Chem.*, Dec. 1, 2007; 45(23): 5618-5625. Available online Oct. 22, 2007.
Afroz et al., "Photo-Removable Protecting Groups for in Situ DNA Microarray Synthesis," *Clin. Chem.*, Oct. 2004; 50(10): 1936-1939.
Agard et al., "A strain-promoted [3+2] azide-alkyne cycloaddition for covalent modification of biomolecules in living systems," *J. Am. Chem. Soc.*, Nov. 24, 2004; 126(46): 15046-15047; published on Web Nov. 2, 2004.
Angiolini et al., "Cross-linked polystyrene resins containing triorganotin-4-vinylbenzoates: Assessment of their catalytic activity in transesterification reactions," *J. Organometallic Chem.*, Jun. 15, 2006; 691(13): 3043-3052. Available online Mar. 14, 2006.
Baskin et al., "Copper-free click chemistry for dynamic in vivo imaging,"*Proc. Natl. Acad. Sci. USA*, Oct. 23, 2007; 104(43): 16793-16797. Available online Oct. 17, 2007.
Baskin et al., "Bioorthogonal Click Chemistry: Covalent Labeling in Living Systems," *QSAR Comb. Sci.*, Dec. 2007; 26(11-12): 1211-1219. Available online Oct. 22, 2007.

Becer et al., "Click Chemistry beyond Metal-Catalyzed Cycloaddition," *Angew. Chem. Int. Ed.*, Jun. 22, 2009; 48(27): 4900-4908. Available online May 27, 2009.
Begum et al., "Autocatalytic Alkyne Cycloadditions: Evidence for Collodial Pt Catalysis," *J. Am. Chem. Soc.*, Oct. 5, 2005; 127(39): 13494-13495. Available online Sep. 13, 2005.
Blawas et al., "Protein patterning,"*Biomaterials*, Apr. 1998; 19(7-9): 595-609.
Boons, "Elucidating structure-function relationships of lipid A: A synthetic approach," Grant Description. Grant No. 5-R01-GM061761-07. National Institute of Health [online]. Project dates Jul. 1, 2000 to Jul. 31, 2010. [Retrieved from the Internet on Aug. 22, 2011] Available online: <URL: http://datalab-1.ics.uci.edu/nih/crisp/2007/getdoc.php?did=46686>, 3 pgs.
Breinbauer et al., "Azide-Alkyne Coupling: A Powerful Reaction for Bioconjugate Chemistry," *Chembiochem.*, Nov. 7, 2003; 4(11): 1147-1149.
Brunner et al., "New porphyrin platinum conjugates for the cytostatic and photodynamic tumor therapy," *Inorganica Chiica Acta*, Jul. 4, 2003; 350: 39-48. Available online May 22, 2003.
Carroll et al., "Photons to illuminate the universe of sugar diversity through bioarrays," *Glycoconj. J.*, Jan. 2008; 25(1): 5-10. Available online Jul. 4, 2007.
Chapman et al., "Acenaphthyne," *J. Am. Chem. Soc.*, Nov. 1981; 103(23): 7033-7036.
Chen et al., "Cell shape provides global control of focal adhesion assembly,"*Biochem. Biophys. Res. Commun.*, Jul. 25, 2003; 307(2): 355-361.
Chiang et al., "Reactive species: Ynols and Ynamines,"*J. Phys. Org. Chem.*, Jun. 1996; 9(6): 361-370.
Chiellini et al., "Patterning of Polymeric Hydrogels for Biomedical Applications," *Macromol. Rapid. Commun.*, Oct. 2001; 22(15): 1284-1287. Available online Oct. 17, 2001.
Choi et al., "Micropatterning of biomolecules on glass surfaces modified with various functional groups using photoactivatable biotin," *Anal. Biochem.*, Dec. 1, 2005; 347(1): 60-66. Available online Sep. 28, 2005.
Codelli et al., "Second-Generation Difluorinated Cyclooctynes for Copper-Free Click Chemistry," *J. Am. Chem. Soc.*, Aug. 27, 2008; 130(34): 11486-11493. Available online Aug. 5, 2008.
Crawford et al., "Antibody Array Technology: Screening and Profiling Protein Expression in Human Cancer Serum using Antibody Array Technologies," [online]. *SIGMA Life Science Innovations*, 2008; (24): 10-3. [Retrieved from the Internet on Aug. 25, 2011.] Available online at: <URL: http://www.sigmaaldrich.com/etc/medialib/flashapps/life-science-innovations/pdfs/lsiweb24-pdf.Par.0001.File.dat/lsiweb24.pdf>.
Dehmlow et al., "Cyclopropenonchemie, X. 2-Alkoxy-3-alkylcyclopropenone," *Chem. Ber.*, Mar. 1988; 121(3): 569-571 (English language abstract). Available online Jan. 23, 2006.

(Continued)

*Primary Examiner* — Susannah Chung
(74) *Attorney, Agent, or Firm* — Mueting, Raasch & Gebhardt, P.A.

(57) ABSTRACT

Cyclic alkynes (e.g., cyclooctynes such as dibenzocyclooctynes) can be photochemically generated from cyclopropenones as disclosed herein. The cyclic alkynes can be reacted (e.g., in situ) with materials having alkyne-reactive groups (e.g., azide groups in a "click" reaction). In preferred embodiments, the generation and reaction of the cyclic alkyne can proceed in the absence of a catalyst (e.g., Cu(I)). These reactions can be useful, for example, for the selective labeling of living cells that are metabolically modified with azido-containing surface monosaccharides, or for light-directed surface patterning.

44 Claims, 13 Drawing Sheets

OTHER PUBLICATIONS

Delehanty et al., "A Microarray Immunoassay for Simultaneous Detection of Proteins and Bacteria," *Anal. Chem.*, Nov. 1, 2002; 74(21): 5681-5687. Available online Oct. 1, 2002.

Dillmore et al., "A Photochemical Method for Patterning the Immobilization of Ligands and Cells to Self-Assembled Monolayers," *Langmuir*, Aug. 17, 2004; 20(17): 7223-7231; published on Web Jul. 24, 2004.

Ellis-Davies, "Caged Compounds: photorelease technology for control of cellular chemistry and physiology," *Nat. Methods*, Aug. 2007; 4(8): 619-628.

Ess et al., "Transition states of strain-promoted metal-free click chemistry: 1,3-dipolar cycloadditions of phenyl azide and cyclooctynes," *Organic Letters*, Apr. 17, 2008; 10(8): 1633-1636. Available online Mar. 26, 2008.

Fernández-Suárez et al., "Redirecting lipoic acid ligase for cell surface protein labeling with small-molecule probes," *Nat. Biotechnol.*, Dec. 2007; 25(12): 1483-1487. Available online Dec. 2, 2007.

Fleischmann et al., "Modification of Polymer Surfaces by Click Chemistry," *Macromolecular Rapid Communications*, Jul. 1, 2008; 29(12-13): 1177-1185. Available online May 27, 2008.

Fournier et al., "Clicking polymers: a straightforward approach to novel macromolecular architectures," *Chem. Soc. Rev.*, Aug. 2007; 36(8): 1369-1380. Available online May 3, 2007.

Furniss et al., *Vogel's Textbook of Practical Organic Chemistry, 5th Ed. Supp.*, Longman Scientific and Technical Ltd, Harlow, England, 1991, 809-816.

Ganesan et al., "Simple micropatterning of biomolecules on a diazoketo-functionalized photoresist," *J. Mater. Chem.*, 2008; 18(6): 703-709. Available online Jan. 7, 2008.

Gramlich et al., "Postsynthetic DNA modification through the copper-catalyzed azide-alkyne cycloaddition reaction," *Angew. Chem. Int. Ed. Engl.*, Oct. 20, 2008; 47(44): 8350-8358.

Hegedus, *Transition Metals in the Synthesis of Complex Organic Molecules*, Sausalito, California, 1994. Cover page, copyright page, and table of contents; 6 pgs.

Heller, "Electrical wiring of redox enzymes," *Acc. Chem. Res.*, May 1990; 23(5): 128-134.

Himo et al., "Copper(I)-catalyzed synthesis of azoles. DFT study predicts unprecedented reactivity and intermediates," *J. Am. Chem. Soc.*, Jan. 12, 2005; 127(1): 210-216. Available online Dec. 8, 2004.

Inglis et al., "Ultrafast click conjugation of macromolecular building blocks at ambient temperature," *Angew. Chem. Int. Ed. Engl.*, Mar. 16, 2009; 48(13): 2411-2414. Available online Feb. 18, 2009.

Johnson et al., "Copper-free click chemistry for the in situ crosslinking of photodegradable star polymers," *Chem. Commun. (Camb.)*, Jul. 14, 2008; (26): 3064-3066. Available online Apr. 24, 2008.

Johnsson, "Visualizing biochemical activities in living cells," *Nat. Chem. Biol.*, Feb. 2009; 5(2): 63-65.

Kolb et al., "Click Chemistry: Diverse Chemical Function from a Few Good Reactions," *Angew. Chem. Int. Ed.*, Jun. 1, 2001; 40(11): 2004-2021. Available online May 28, 2001.

Kolb et al., "The growing impact of click chemistry on drug discovery," *Drug Discov. Today*, Dec. 15, 2003; 8(24): 1128-1137.

Ku et al., "Surface patterning with fluorescent molecules using click chemistry directed by scanning electrochemical microscopy," *J. Am. Chem. Soc.*, Feb. 27, 2008; 130(8): 2392-2393. Available online Feb. 2, 2008.

Kuzmanich et al., "Solid-State Photodecarbonylation of Diphenylcyclopropenone: A Quantum Chain Process Made Possible by Ultrafast Energy Transfer," *J. Am. Chem. Soc.*, Jan. 30, 2008; 130(4): 1140-1141. Available online Jan. 10, 2008.

Kuzmanich et al., "Photonic Amplification by a Singlet-State Quantum Chain Reaction in the Photodecarbonylation of Crystalline Diarylcyclopropenones," *J. Am. Chem. Soc.*, 2009; 131(32): 11606-11614. Available online Jul. 28, 2009.

Kuzmin et al., "Dual reactivity of a photochemically-generated cyclic enyne-allene," *Chem. Commun. (Camb.)*, Oct. 14, 2009; (38): 5707-5709. Available online Aug. 14, 2009.

Lallana et al., "Surpassing the use of copper in the click functionalization of polymeric nanostructures: a strain-promoted approach," *J. Am. Chem. Soc.*, Apr. 29, 2009; 131(16): 5748-5750; published on Web Apr. 6, 2009.

Laughlin et al., "In vivo imaging of membrane-associated glycans in developing zebrafish," *Science*, May 2, 2008; 320(5876): 664-667.

Laughlin et al., "Imaging the glycome," *Proc. Natl. Acad. Sci. USA*, Jan. 6, 2009; 106(1): 12-17. Available online Dec. 22, 2008.

Li et al., "Synthesis of Novel Heterobifunctional Isocyanato Cross-Linkers and Their Applications for the Preparation of 10-Hydroxycamptothecin and SN-38 Conjugates with Melanotransferrin P97," *Synth. Comm.*, 2007; 37(11): 1899-1915. Available online Jun. 30, 2007.

Locklin et al., "Smart Autonomous Nanomotors through Orthogonal Self-Assembly," Grant Abstract. Grant No. ECCS 0901141 [online]. National Science Foundation. Project Dates: Aug. 1, 2009 to Jul. 31, 2012. Available online: URL:<http://www.nsf.gov/awardsearch/showAward.do?AwardNumber=0901141>, 2 pgs.

Lundberg et al., "Click Assisted One-Pot Multi-Step Reactions in Polymer Science: Accelerated Synthetic Protocols," *Macromol. Rapid. Comm.*, Jul. 1, 2008; 29(12-13): 998-1015. Available online Jun. 10, 2008.

Lutz, "1,3-dipolar cycloadditions of azides and alkynes: a universal ligation tool in polymer and materials science," *Angew. Chem. Int. Ed. Engl.*, Feb. 5, 2007; 46(7): 1018-1025. Available online Jan. 9, 2007.

MacBeath et al., "Printing Proteins as Microarrays for High-Throughput Function Determination," *Science*, Sep. 8, 2000; 289(5485): 1760-1763.

Matyjaszewski et al., "Polymers at Interfaces: Using Atom Transfer Radical Polymerization in the Controlled Growth of Homopolymers and Block Copolymers from Silicon Surfaces in the Absence of Untethered Sacrificial Initiator," *Macromolecules*, 1999; 32(26): 8716-8724. Available online Dec. 10, 1999.

Mayer et al., "Biologically active molecules with a 'light switch,'" *Angew. Chem. Int. Ed. Engl.*, Jul. 24, 2006; 45(30): 4900-4921. Available online Jul. 7, 2006.

McGlennen, "Miniaturization Technologies for Molecular Diagnostics," *Clin. Chem.*, Mar. 2001; 47(3) 393-402.

Michael et al., "On the Formation of Imido-1,2-Diazol Derivatives from Aromatic Azimides and Esters of Acetylenecarboxylic Acids," *Am. Chem. J.*, 1898; 20(7): 377-395.

Michel et al., "Carbohydrate microarrays by microcontact 'click' chemistry," *Langmuir*, Nov. 4, 2008; 24(21): 12116-12118. Available online Oct. 7, 2008.

Mita et al., "Photochemistry in polymer solids. 9. Photoisomerization of azobenzene in a polycarbonate film," *Macromolecules*, Feb. 1989; 22(2): 558-563.

Morais et al., "DNA microarraying on compact disc surfaces. Application to the analysis of single nucleotide polymorphisms in Plum pox virus," *Chem. Commun. (Camb.)*, Jun. 14, 2006; (22): 2368-2370. Available online May 2, 2006.

Moses et al., "The growing applications of click chemistry," *Chem. Soc. Rev.*, Aug. 2007; 36(8): 1249-1262. Available online May 3, 2007.

Murata et al., "Photochemistry of 1,3-bis(diazo)indan-2-one: consecutive decomposition and suppression of a Wolff rearrangement," *J. Am. Chem. Soc.*, May 1993; 115(10): 4013-4023.

Nakajima, "Patterning of Protein on the Macrochannel Wall," *J. Flow. Inj. Anal.*, 2006; 23(2): 123.

Nandivada et al., "Click Chemistry: Versatility and Control in the Hands of Materials Scientists," *J. Adv. Mater.*, Sep. 2007; 19(17): 2197-2208. Available online Aug. 9, 2007.

Ning et al., "Visualizing Metabolically Labeled Glycoconjugates of Living Cells by Copper-Free and Fast Huisgen Cycloadditions," *Angew. Chem. Int. Ed. Engl.*, Mar. 7, 2008; 47(12): 2253-2255. Available online Feb. 14, 2008.

Nozaki et al., "Mechanistic Aspects of the Alternating Copolymerization of Propene with Carbon Monoxide Catalyzed by Pd(II) Complexes of Unsymmetrical Phosphine—Phosphite Ligands," *J. Am. Chem. Soc.*, 1997; 119(52): 12779-12795. Available online Dec. 31, 1997.

Ochiai et al., "Expeditious Chemoenzymatic Synthesis of Homogenous N-Glycoproteins Carrying Defined Oligosaccharide Ligands," *J. Am. Chem. Soc.*, 2008; 130(41): 13790-13803. Available online Sep. 20, 2008.

Orski et al., "High Density Scaffolding of Functional Polymer Brushes: Surface Initiated Atom Transfer Radical Polymerization of Active Esters," *Langmuir*, 2010; 26(3): 2136-2143. Available online Oct. 2, 2009.

Orski et al., "High Density Orthogonal Surface Immobilization via Photoactivated Copper-Free Click Chemistry," *J. Am. Chem. Soc.*, Aug. 18, 2010; 132(32): 11024-11026; published on Web Jul. 22, 2010.

Panda et al., "An array of insights: application of DNA chip technology in the study of cell biology," *Trends Cell Biol.*, Mar. 2003; 13(3): 151-156. Available online Jan. 31, 2003.

Pandithavidana et al., "Photochemical Generation and Reversible Cycloaromatization of a Nine-Membered Ring Cyclic Enediyne," *J. Am. Chem. Soc.*, Jan. 14, 2009; 131(1): 351-356. Available online Dec. 3, 2008.

Pelliccioli et al., "Photoremovable protecting groups: reaction mechanisms and applications," *Photochem. Photobiol. Sci.*, Jul. 2002; 1(7): 441-458. Available online Jun. 6, 2002.

Penoni et al., "On the mechanism of nitrosoarene-alkyne cycloaddition," *J. Am. Chem. Soc.*, Jan. 21, 2009; 131(2): 653-661; published on Web Dec. 18, 2008.

Poloukhtine et al., "Highly Efficient Photochemical Generation of a Triple Bond: Synthesis, Properties, and Photodecarbonylation of Cyclopropenones," *J. Org. Chem.*, Oct. 3, 2003; 68(20): 7833-7840. Available online Sep. 9, 2003.

Poloukhtine et al., "Photoswitchable enediynes: use of cyclopropenone as photocleaveable masking group for the enediyne triple bond," *Chem. Commun.*, Feb. 7, 2005; 617-619. Available online Dec. 10, 2004.

Poloukhtine et al., "Application of photochemical decarbonylation of cyclopropenones for the in situ generation of reactive enediynes. Construction of a cyclopropenone-containing enediyne precursor by using a cyclopropenone acetal building block," *J. Org. Chem.*, Feb. 18, 2005; 70(4): 1297-1305.

Poloukhtine et al., "Mechanism of the cyclopropenone decarbonylation reaction. A density functional theory and transient spectroscopy study," *J. Phys. Chem. A*, Feb. 9, 2006; 110(5): 1749-1757.

Poloukhtine et al., "Two-photon photochemical generation of reactive enediyne," *J. Org. Chem.*, Sep. 15, 2006; 71(19):7417-7421; published on Web Aug. 16, 2006.

Poloukhtine et al., "Selective Labeling of Living Cells by a Photo-Triggered Click Reaction," *J. Am. Chem. Soc.*, Nov. 4, 2009;131(43): 15769-15776. Available online Oct. 8, 2009.

Popik, "Career: Towards Space- and Time-resolved Generation of p-Benzyne Diradical: Development of Photoswitchable Analogs of Natural Enediyne Antibiotics," Grant Abstract. Grant No. CHE 0449478. National Science Foundation [online]. Retrieved on Aug. 22, 2011. Available online at URL: <http://www.nsf.gov/awardsearch/showAward.do?AwardNumber=0449478>, 2 pgs.

Popper et al., "Proteomics—Tissue and Protein Microarrays and Antibody Array: what information is provided?" *Arch. Path. & Lab. Med.*, Oct. 2008; 132(10): 1570-1572.

Rostovtsev et al., "A stepwise huisgen cycloaddition process: copper(I)-catalyzed regioselective 'ligation' of azides and terminal alkynes," *Angew. Chem. Int. Ed. Engl.*, Jul. 15, 2002; 41(14): 2596-2599.

Saxon et al., "Cell surface engineering by a modified Staudinger reaction," *Science*, Mar. 17, 2000; 287(5460): 2007-2010.

Sekkat et al., "Photoreactive Organic Thin Films," Academic Press, Waltham, Massachussetts, 2002. Cover page, copyright page, and table of contents. 12 pgs.

Sgouras et al., "Methods for the evaluation of biocompatibility of soluble synthetic polymers which have potential for biomedical use: 1—Use of the tetrazolium-based colorimetric assay (MTT) as a preliminary screen for evaluation of in vitro cytotoxicity," *J. Mater. Sci.: Mater. Med.*, 1990; 1(2): 61-68.

Sharpless et al., "In situ click chemistry: a powerful means for lead discovery," *Exp. Opin. Drug Discov.*, Nov. 2006; 1(6): 525-538.

Sletten et al., "A Hydrophilic Azacyclooctyne for Cu-Free Click Chemistry," *Org. Lett.*, Jul. 17, 2008, 10(14):3097-3099. Available online Jun. 13, 2008.

Song et al., "Selective Functionalization of a Genetically Encoded Alkene-Containing Protein Via 'Photoclick Chemistry' in Bacterial Cells," *J. Am. Chem. Soc.*, Jul. 30, 2008;130(30): 9654-9655. Available online Jul. 2, 2008.

Speers et al., "Activity-Based Protein Profiling in Vivo Using a Copper(I)-Catalyzed Azide-Alkyne [3+2] Cycloaddition," *J. Am. Chem. Soc.*, Apr. 23, 2003; 125(16): 4686-4687; published on Web Mar. 28, 2003.

Strable et al., "Unnatural amino acid incorporation into virus-like particles," *Bioconjugate Chem.*, Apr. 2008; 19(4): 866-875. Available online Mar. 5, 2008.

Sun et al., "Carbohydrate and protein immobilization onto solid surfaces by sequential Diels-Alder and azide-alkyne cycloadditions," *Bioconjugate Chem.*, Jan.-Feb. 2006; 17(1): 52-57; published on Web Dec. 21, 2005.

Tornøe et al., "Peptidotriazoles on Solid Phase: [1,2,3]-Triazoles by Regiospecific Copper(I)-Catalyzed 1,3-Dipolar Cycloadditions of Terminal Alkynes to Azides," *J. Org. Chem.*, May 3, 2002; 67(9): 3057-3064. Available online Apr. 2, 2002.

Urdabayev et al., "Two-photon induced photodecarbonylation reaction of cyclopropenones," *Chem. Commun. (Camb.)*, Jan. 28, 2006; (4): 454-456.

Van Eyk et al., "Chapter 8. Antibody Microarrays for Protein and Glycan Detection," in *Clinical Proteomics: From Diagnosis to Therapy*, Wiley-VCH Verlag GmbH and Co. KGaA, Berlin, Germany, 2008, 101-111.

von Maltzahn et al., "In vivo tumor cell targeting with 'click' nanoparticles," *Bioconjugate Chem.*, Aug. 2008; 19(8): 1570-1578. Available online Jul. 9, 2008.

Wang et al., "Bioconjugation by Copper(I)-Catalyzed Azide-Alkyne [3+2] Cycloaddition," *J. Am. Chem. Soc.*, Mar. 19, 2003; 125(11): 3192-3193. Available online Feb. 22, 2003.

Weisbrod et al., "Novel strategies for the site-specific covalent labelling of nucleic acids," *Chem. Commun. (Comb.)*, Nov. 30, 2008; (44): 5675-5685. Available online Sep. 25, 2008.

Huisgen. "Kinetics and Mechanism of 1,3-Dipolar Cycloadditions". 1963. *Angewandte Chemie International Edition*. 2(11):633-645. 14 pages total.

Huisgen. "1,3-Dipolar Cycloadditions, Past and Future". *Angewandte Chemie International Edition*. 2(10):565-598. 35 pages total, 1963.

Biotin (from Wikipedia). Retrieved on Jan. 19, 2012. Retrieved from the Internet: http://en.wikipedia.org/wiki/Biotin. 8 pages; last modified Jan. 15, 2012.

Polyethylene Glycol (from Wikipedia). Retrieved on Jan. 19, 2012. Retrieved from the Internet: http://en.wilipedia.org/wiki/Polyethylene_glycol. 8 pages; last modified Jan. 19, 2012.

\* cited by examiner

*Fig.* 6
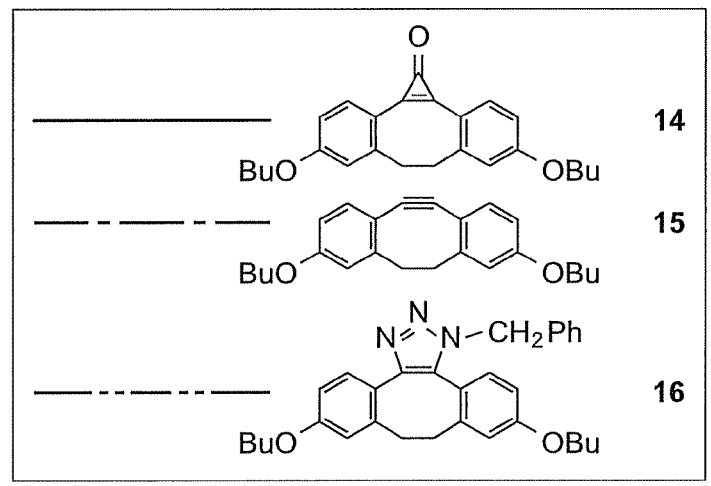
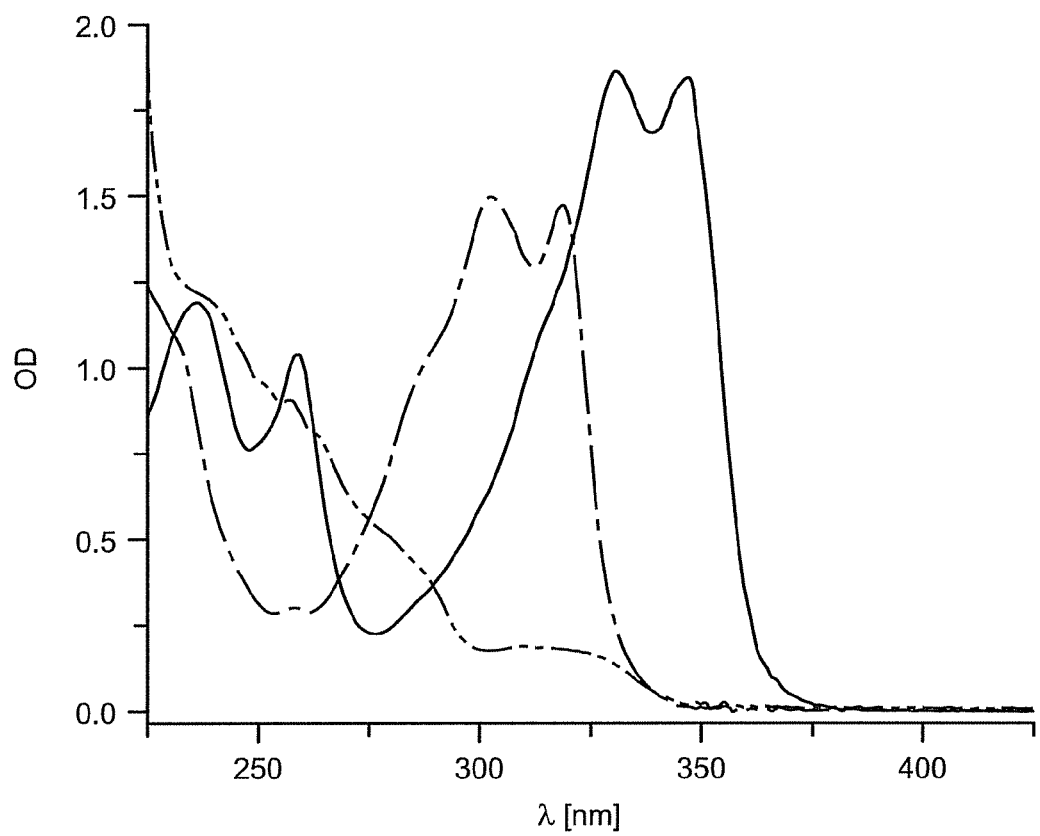

CYCLOPROPENONES AND THE PHOTOCHEMICAL GENERATION OF CYCLIC ALKYNES THEREFROM

This application claims the benefit of U.S. Provisional Application Ser. Nos. 61/153,762, filed Feb. 19, 2009, and 61/238,835, filed Sep. 1, 2009, both of which are herein incorporated by reference in their entireties.

GOVERNMENT RIGHTS

The present invention was made with support from the National Science Foundation under Grant No. CHE0449478, and the National Institutes of Health Grant Nos. CA88986 and GM 61761. The U.S. government has certain rights in this invention.

BACKGROUND

Connection (or ligation) of two fragments to make a larger molecule or structure is often achieved with the help of the so-called "click chemistry". This term is used to describe a set of bimolecular reactions that meet the following criteria: reactions should be wide in scope but selective; produce high yield of the product, proceed with reasonable rate under mild conditions; and tolerate broad range of solvents. Among known click reactions is the reaction of azides with acetylenes. The formation of 1,2,3-triazoles in 1,3-dipolar cycloaddition of azides to triple bond is known, but because the activation energy of acetylene-azide cycloaddition is relatively high ($\Delta G^{\ddagger}$ approximately 26 kcal/mol), the reaction is very slow under ambient conditions.

The utility of the reaction of azides with alkynes was expanded by the discovery of Cu (I) catalysis. 1,3-cycloaddition of azides to terminal acetylenes in the presence of catalytic amounts of cuprous salts is facile at room temperature in organic or aqueous solutions. The copper-catalyzed version of the acetylene-azide cycloaddition (a.k.a. azide click reaction) found a broad range of applications from microelectronics to virus labeling, to drug development. However, the use of cytotoxic Cu (I) catalyst has largely precluded application of this click reaction in living systems.

Catalyst-free 1,3-dipolar cycloaddition of azides to cyclooctynes has made possible a bio-compatible version of the azide click reaction. The triple bond incorporated in an eight-membered ring is apparently already bent into the transition state-resembling geometry, thus reducing the activation barrier.

Besides biocompatibility, another major bottleneck in the application of chemical reporters in living system is the lack of spatial and temporal resolution. Photochemical immobilization of carbohydrates, proteins, DNA fragments, antibodies, and other substrates allows for the formation of patterned or gradient arrays on various surfaces. These techniques are widely used in the development of novel high throughput analytical methods. Due to good compatibility of azide click chemistry with various biological substrates, and the robustness of the triazole linker, it has been employed in surface functionalization including, for example, carbohydrate and protein immobilization. However, this immobilization technique was not amenable to patterned modification of the surface. Although SEM-directed electrochemical reduction of Cu(II) to Cu(I) allows the patterning of fluorescent molecules on a glass slide, this method is of limited in scope and practicality.

New methods for ligating fragments to make a larger molecule or structure are needed in the art.

SUMMARY

The present disclosure is generally related to methods for light-induced ligation of molecules, preferably without the use of a catalyst. In particular, the disclosure relates to the generation of reactive acetylenes produced by the light-induced decarbonylation of cyclopropenones as disclosed herein. The photochemical ligation method of the present disclosure provides a method of linking two molecules triggered by the photochemical generation of cyclic alkynes (e.g., cyclooctynes) from corresponding cyclopropenones.

In one aspect, the present disclosure provides cyclopropenones and methods of photochemically inducing the reaction of two materials using the cyclopropenones. In one embodiment, the method includes: photochemically generating a cyclic alkyne from a cyclopropenone; and contacting the cyclic alkyne with a material including an alkyne-reactive group (e.g., a 1,3-dipole-functional compound) under conditions effective for the cyclic alkyne and the material including the alkyne-reactive group to react. In some embodiments, the method photochemically induces the ligation of the cyclic alkyne and the material including the alkyne-reactive group through the formation, for example, of a cyclic adduct (e.g., a heterocyclic compound), preferably without the use of a catalyst (e.g., a metal-containing catalyst).

In one embodiment, the cyclopropenone has the formula:

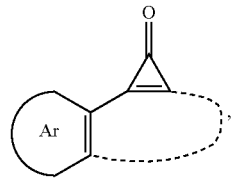

wherein Ar is a group representing a monocyclic or polycyclic, aromatic or heteroaromatic ring, and the dashed line represents a four atom bridge. In certain embodiments, the four atom bridge includes carbon atoms, oxygen atoms, nitrogen atoms, phosphorus atoms, or combinations thereof.

In another embodiment, the cyclopropenone has the formula:

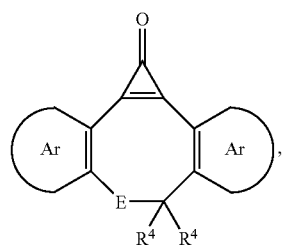

wherein each Ar is a group independently representing a monocyclic or polycyclic, aromatic or heteroaromatic ring; E represents $NR^6$, $^+N(R^6)_2$, S, S=O, $SO_2$, O, $PR^6$, or $C(R^4)_2$; each $R^4$ is independently selected from the group consisting of hydrogen, halogen, hydroxy, alkoxy, nitrate, nitrite, sulfate, a C1-C10 organic group, and a linking group; and each $R^6$ is independently hydrogen, a C1-C10 organic group, and/ or a linking group. Linking groups can be useful, for example, for attaching substrates and/or tags.

In another embodiment, the cyclopropenone have the formula:

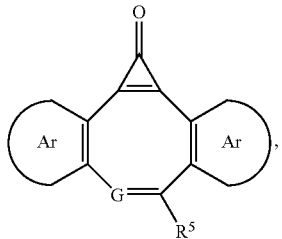

wherein each Ar is a group independently representing a monocyclic or polycyclic, aromatic or heteroaromatic ring; G represents $CR^6$, N, or P; and each $R^5$ and $R^6$ is independently selected from the group consisting of hydrogen, halogen, hydroxy, alkoxy, nitrate, nitrite, sulfate, a C1-C10 organic group, and a linking group. Linking groups can be useful, for example, for attaching substrates and/or tags.

In another embodiment, the cyclopropenone have the formula:

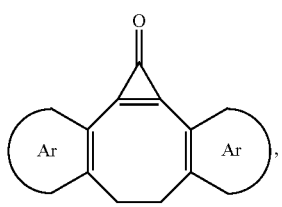

wherein each Ar is a group independently representing a monocyclic or polycyclic, aromatic or heteroaromatic ring.

In certain embodiments, the photochemically generated cycloalkynes may then undergo a facile "strain-promoted" cycloaddition reaction with at least one 1,3-dipole-functional compound (e.g., an azide-functional compound, a nitrile oxide-functional compound, a nitrone-functional compound, an azoxy-functional compound, and/or an acyl diazo-functional compound) to form a heterocyclic compound, preferably in the absence of added catalyst (e.g., Cu(I)). Significantly and advantageously for the use of the products in in vivo studies, for example, the cyclopropenone precursor itself does not react with 1,3-dipole-functional compound (e.g., azide functional compounds) in the absence of light, and are stable.

Thus, in another aspect, the present disclosure provides a method of photochemically inducing the ligation of two molecules. In one embodiment, the method includes: (a) photochemically generating a cyclic alkyne (e.g., a cyclooctyne) from a cyclopropenone; and (b) contacting the cyclic alkyne with an azide under conditions effective to form a triazole.

In certain embodiments, the cyclopropenone is a dibenzocyclopropenone having the formula I:

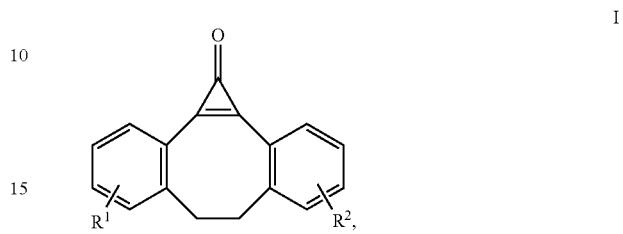

wherein: $R^1$ is selected from the group consisting of: an alkoxy and a hydroxyl; $R^2$ is selected from the group consisting of: an alkyl, a heteroalkyl, a cycloalkyl, a heterocycloalkyl, an aryl, an alkoxy, a carboxy, a hydroxyl, an ether, an ester, and a halogen; and the cyclooctyne is a dibenzocyclooctyne. Alternatively, or in addition to, $R^2$ can be a PEGylated group, a biotinylated group, and/or a group containing an amide or carbamate linker. As used herein, the terms "PEGylated" and "biotinylated" are meant to describe groups that include a polyethylene glycol (PEG) fragment or a biotin fragment, respectively. Optionally at least one of the azide or the cyclooctyne precursor can be bound to the surface of a substrate (e.g., a solid substrate or a cell membrane) and/or integrated into a substrate layer.

In certain embodiments, step (a) includes irradiating the cyclopropenone with light having a wavelength (e.g., 220 nm to about 450 nm) selectively absorbed by the cyclopropenone, and substantially not absorbed by a cyclic alkyne or by a triazole.

In certain embodiments, the method further includes the step of providing a cyclopropenone, said step including: (i) providing a 3,3'-dialkyloxybibenzyl; and (ii) reacting the 3,3'-dialkyloxybibenzyl with tetrachloropenone in the presence of anhydrous aluminum chloride under medium dilution conditions effective to generate a cyclopropenone.

In another aspect, the present disclosure provides cyclopropenones. In one embodiment, the cyclopropenones have the formula:

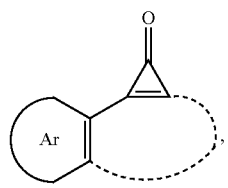

wherein Ar is a group representing a monocyclic or polycyclic, aromatic or heteroaromatic ring, and the dashed line represents a four atom bridge. In certain embodiments, the four atom bridge includes carbon atoms, oxygen atoms, nitrogen atoms, phosphorus atoms, or combinations thereof.

In another embodiment, the cyclopropenones have the formula:

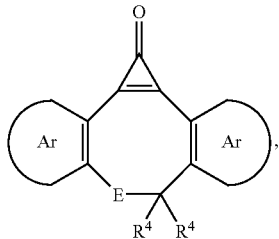

wherein each Ar is a group independently representing a monocyclic or polycyclic, aromatic or heteroaromatic ring; E represents $NR^6$, $^+N(R^6)_2$, S, S=O, $SO_2$, O, $PR^6$, or $C(R^4)_2$; each $R^4$ is independently selected from the group consisting of hydrogen, halogen, hydroxy, alkoxy, nitrate, nitrite, sulfate, a C1-C10 organic group, and a linking group; and each $R^6$ is independently hydrogen, a C1-C10 organic group, and/or a linking group. Linking groups can be useful, for example, for attaching substrates and/or tags.

In another embodiment, the cyclopropenones have the formula:

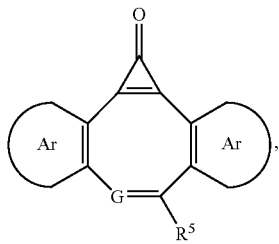

wherein each Ar is a group independently representing a monocyclic or polycyclic, aromatic or heteroaromatic ring; G represents $CR^6$, N, or P; and each $R^5$ and $R^6$ is independently selected from the group consisting of hydrogen, halogen, hydroxy, alkoxy, nitrate, nitrite, sulfate, a C1-C10 organic group, and a linking group. Linking groups can be useful, for example, for attaching substrates and/or tags.

In still another embodiment, the cyclopropenones have the formula:

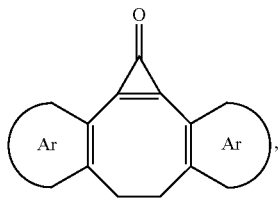

wherein each Ar is a group independently representing a monocyclic or polycyclic, aromatic or heteroaromatic ring. In certain preferred embodiments, the cyclopropenone has the formula I:

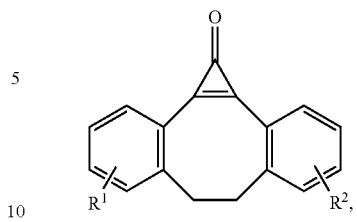

I wherein: $R^1$ is selected from the group consisting of: an alkoxy and a hydroxyl; $R^2$ is selected from the group consisting of: an alkyl, a heteroalkyl, a cycloalkyl, a heterocycloalkyl, an aryl, an alkoxy, a carboxy, a hydroxyl, an ether, an ester, and a halogen; and the cyclooctyne is a dibenzocyclooctyne. Alternatively, or in addition to, $R^2$ can be a PEGylated group, a biotinylated group, and/or a group containing an amide or carbamate linker.

In another aspect, the present disclosure provides a dibenzocyclooctyne of the formula:

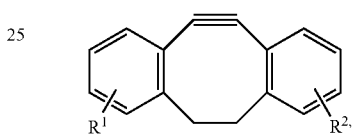

wherein: $R^1$ is selected from the group consisting of: an alkoxy and a hydroxyl; $R^2$ is selected from the group consisting of: an alkyl, a heteroalkyl, a cycloalkyl, a heterocycloalkyl, an aryl, an alkoxy, a carboxy, a hydroxyl, an ether, an ester, and a halogen; and the cyclooctyne is a dibenzocyclooctyne. Alternatively, or in addition to, $R^2$ can be a PEGylated group, a biotinylated group, and/or a group containing an amide or carbamate linker.

In yet another aspect, the present disclosure provides a triazole of the formula:

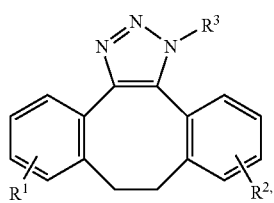

wherein: $R^1$ is selected from the group consisting of: an alkoxy and a hydroxyl; $R^2$ is selected from the group consisting of: an alkyl, a heteroalkyl, a cycloalkyl, a heterocycloalkyl, an aryl, an alkoxy, a carboxy, a hydroxyl, an ether, an ester, and a halogen; and $R^3$ is selected from the group consisting of a primary alkyl, a secondary alkyl, a tertiary alky, an aryl, an alkylaryl, an acyl, an alkylacyl, and an arylacyl. Alternatively, or in addition to, $R^2$ can be a PEGylated group, a biotinylated group, and/or a group containing an amide or carbamate linker.

In other certain embodiments, the photochemically generated cycloalkynes may then undergo cycloaddition reactions (e.g., thermally promoted reactions) with dienes to give Diels-Alder adducts; with nitrosoarenes to give N-hydroxy indoles; with an alkene and a metal carbene complex to give butadiene products (e.g., enyne metathesis); with alkynes and a metal catalyst to give new alkynes (e.g., alkyne metathesis); with other metal-containing compounds such as, for example, four- and/or five-membered platinacycles to give cycloaddition products; with alkenes and carbon monoxide to give [2+2+1] cycloaddition products (e.g., a Pauson Khand reaction); with compounds bearing intermetallic multiple bonds (e.g., ($\eta$-$C_5Me_5$)$_2$Rh$_2$($\mu$-CO)$_2$, [RO]$_3$Mo≡Mo[OR]$_3$, [RCO$_2$]$_2$W≡W[O$_2$CR]$_2$, complexes with double, triple and quadruple metal-metal bond, respectively) to yield, for instance, terminal (M≡CR) or bridged (M=C(R)-M] metal-carbido, or bridging alkyne complexes; and with nitriles, cyanates, isocyanates, and/or isothiocyanates, under the appropriate conditions, to yield the respective metathesis and/or cycloaddition products.

The term "cycloaddition" as used herein refers to a chemical reaction in which two or more pi-electron systems (e.g., unsaturated molecules or unsaturated parts of the same molecule) combine to form a cyclic product in which there is a net reduction of the bond multiplicity. In a cycloaddition, the pi-electrons are used to form new sigma bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 2,3-dipolar cycloadditions, occur between a 1,3-dipole and a dipolarophile and are typically used for the construction of five-membered heterocyclic rings.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

BRIEF DESCRIPTION OF THE DRAWINGS

Further aspects of the present disclosure will be more readily appreciated upon review of the detailed description of its various embodiments, described below, when taken in conjunction with the accompanying figures.

FIG. 6 is a graph illustrating the spectra of (about 5×10$^{-5}$ M) methanol solutions of cyclopropenone 14; acetylene 15; and triazole 16.

Figure 1:
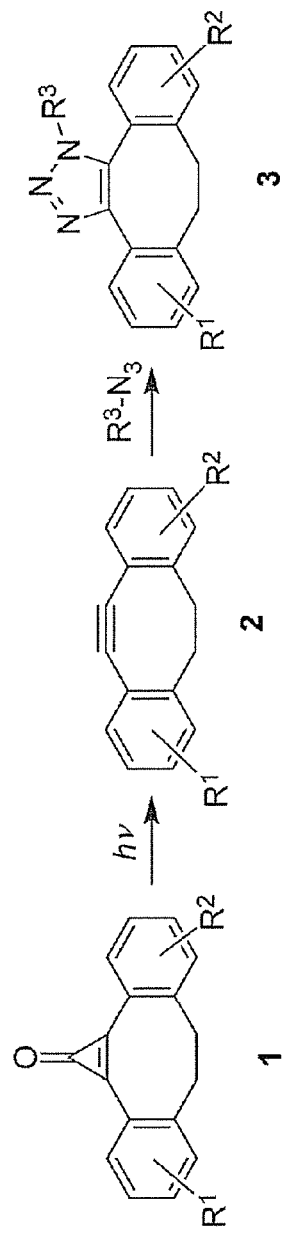
FIG. 1 illustrates a generalized scheme for the photochemical generation of a dibenzocyclooctyne from a cyclopropenone precursor followed by reaction with an azide to produce a triazole.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

DETAILED DESCRIPTION OF ILLUSTRATIVE EMBODIMENTS

The methods of the present disclosure provide for photochemically inducing the reaction of two materials by photochemically generating an activated alkyne (e.g., a cyclooctyne) from a cyclopropenone. The generated cyclic alkyne can react with another material, which in certain embodiments causes ligation of the cyclic alkyne with the other material.

The term "activated alkyne," as used herein, refers to a chemical group that selectively reacts with an alkyne-reactive group, such as an azido group or a phosphine group, on another molecule to form a covalent chemical bond between the activated alkyne group and the alkyne reactive group. Examples of alkyne-reactive groups include azides. "Alkyne-reactive" can also refer to a molecule that contains a chemical group that selectively reacts with an alkyne group. As used herein activated alkyne encompasses any terminal alkynes or cyclic alkynes (dipolarophiles) that will react with 1,3-dipoles such as azides in a facile fashion.

The term "azide reactive," as used herein, refers to a material that selectively reacts with an azido modified group on another molecule to form a covalent chemical bond between the azido modified group and the azide reactive group. Examples of azide-reactive groups include alkynes and phosphines (e.g., triaryl phosphine). "Azide-reactive" can also refer to a molecule that selectively reacts with an azido group.

In certain embodiments, the photochemically generated cycloalkynes may then undergo a facile "strain-promoted" cycloaddition reaction with at least one 1,3-dipole-functional compound (e.g., an azide-functional compound, a nitrile oxide-functional compound, a nitrone-functional compound, an azoxy-functional compound, and/or an acyl diazo-functional compound) to form a heterocyclic compound, preferably in the absence of added catalyst (e.g., Cu(I)). Significantly and advantageously for the use of the products in in vivo studies, for example, the cyclopropenone precursor itself does not react with 1,3-dipole-functional compound (e.g., azide functional compounds) in the absence of light, and are stable, capable of withstanding prolonged heating).

In other certain embodiments, the photochemically generated cycloalkynes may then undergo cycloaddition reactions (e.g., thermally promoted reactions) with dienes to give Diels-Alder adducts; with nitrosoarenes to give N-hydroxy indoles; with an alkene and a metal carbene complex to give butadiene products (e.g., enyne metathesis); with alkynes and a metal catalyst to give new alkynes (e.g., alkyne metathesis); with other metal-containing compounds such as, for example, four- and/or five-membered platinacycles to give cycloaddition products; and with alkenes and carbon monoxide to give [2+2+1] cycloaddition products (e.g., a Pauson Khand reaction).

The methods encompassed by the present disclosure may be useful for generating surfaces, modified with cyclopropenone-containing compounds, which may be used for the patterned immobilization of a broad range of biomolecules.

The present disclosure provides a method of photochemically inducing the ligation of two molecules, the method including: (a) photochemically generating a cyclic alkyne (e.g., a cyclooctyne) from a cyclopropenone; and (b) contacting the cyclic alkyne with an azide under conditions effective to form a triazole.

In some embodiments, the cyclopropenones have the formula:

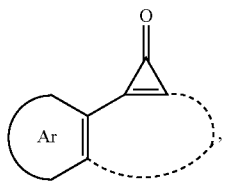

wherein Ar is a group representing a monocyclic or polycyclic, aromatic or heteroaromatic ring, and the dashed line represents a four atom bridge. In certain embodiments, the four atom bridge includes carbon atoms, oxygen atoms, nitrogen atoms, phosphorus atoms, or combinations thereof. Such cyclopropenones can be prepared, for example, by the addition of a dihalocarbene to a corresponding cyclic alkyne followed by hydrolysis in methods similar to those further described herein below.

Figure 14:
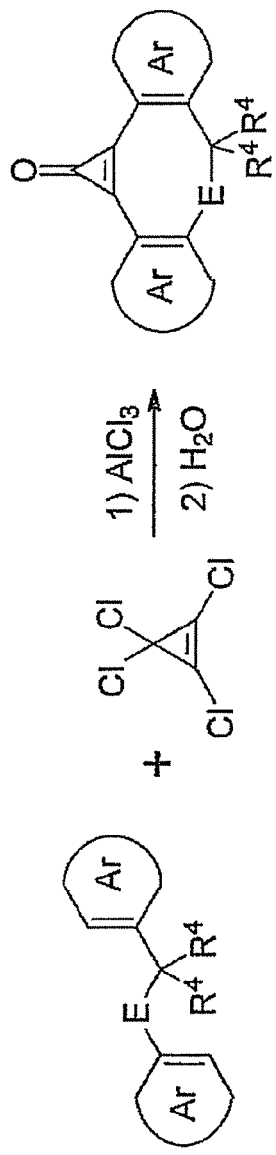
FIGS. 14-16 illustrate exemplary methods for preparing cyclopropenones as further described herein.
Figure 15:
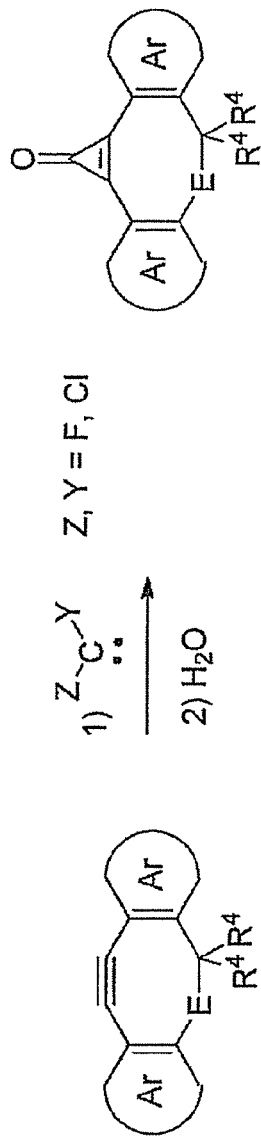

In another embodiment, the cyclopropenones have the formula:

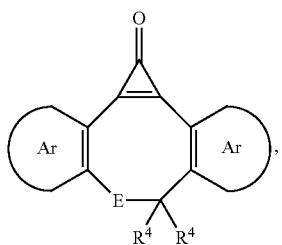

wherein each Ar is a group independently representing a monocyclic or polycyclic, aromatic or heteroaromatic ring; E represents $NR^6$, $^+N(R^6)_2$, S, S=O, $SO_2$, O, $PR^6$, or $C(R^4)_2$; each $R^4$ is independently selected from the group consisting of hydrogen, halogen, hydroxy, alkoxy, nitrate, nitrite, sulfate, a C1-C10 organic group, and a linking group; and each $R^6$ is independently hydrogen, a C1-C10 organic group, and/or a linking group. Linking groups can be useful, for example, for attaching substrates and/or tags. In some embodiments, such cyclopropenones can be prepared, for example, via a double Friedel-Crafts alkylation as illustrated, for example, in FIG. 14. In other embodiments, such cyclopropenones can be prepared, for example, by the addition of a dihalocarbene to a corresponding cyclic alkyne followed by hydrolysis as illustrated, for example, in FIG. 15. See, for example, Poloukhtine et al., *Chemical Communications* 2005, 617-619; and Kuzmin et al., *Chemical Communications* 2009, 5707-5709. See, also, Poloukhtine et al., *Journal of Organic Chemistry* 2005, 70(4):1297-1305.

Figure 16:
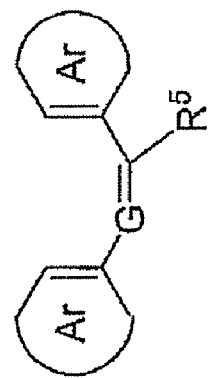

In another embodiment, the cyclopropenones have the formula:

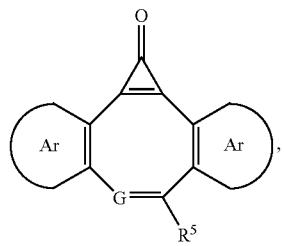

wherein each Ar is a group independently representing a monocyclic or polycyclic, aromatic or heteroaromatic ring; G represents $CR^6$, N, or P; and each $R^5$ and $R^6$ is independently selected from the group consisting of hydrogen, halogen, hydroxy, alkoxy, nitrate, nitrite, sulfate, a C1-C10 organic group, and a linking group. Linking groups can be useful, for example, for attaching substrates and/or tags. In some embodiments, such cyclopropenones can be prepared, for example, via a double Friedel-Crafts alkylation as illustrated, for example, in FIG. 16.

In another embodiment, the cyclopropenone has the formula:

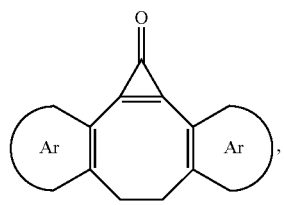

wherein each Ar is a group independently representing a monocyclic or polycyclic, aromatic or heteroaromatic ring.

As used herein, the term "organic group" is used for the purpose of this disclosure to mean a hydrocarbon group that is classified as an aliphatic group, cyclic group, or combination of aliphatic and cyclic groups (e.g., alkaryl and aralkyl groups). In the context of the present disclosure, suitable organic groups for cyclopropenones and compounds having alkyne reactive groups as disclosed herein are those that do not interfere with the photochemical generation of the cyclic alkyne or the reaction of the cyclic alkyne with a compound having an alkyne reactive group. In the context of the present disclosure, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the teen "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The term azide as used herein refers to organic azides having the general formula R—$N_3$ where R is an organic group selected from the group consisting of alkyl, alkyl amino, nitrogen-containing heterocyclic-substituted alkyl (that is, an alkyl group substituted with at least one nitrogen-containing heterocycle), and alkyl amine substituted with at least one alkyl azide group. Non-limiting examples of alkyl groups include methyl, ethyl, propyl, butyl, and isomers (iso-, sec-, tert-, etc.) thereof. Non-limiting examples of alkyl amino groups include dimethylamino, diethylamino, dipropylamino, dibutylamino, and isomers thereof, as well as "mixed" alkyl amino groups, e.g., N-methyl, N-ethylamino; N-propyl, N-butylamino; etc.; and isomers thereof. Non-limiting examples of nitrogen-containing heterocyclic-substituted alkyl groups include alkyl groups substituted with pyrrolidine, imidazole, pyrrole, piperidine, pyrroline, pyrazole, piperazine, or 1,2,4-triazole. When R is an "alkyl amine substituted with at least one alkyl azide group" the organic azide has the formula $R^1NH(R^2N_3)$ or $R^1N(R^2N_3)(R^3N_3)$, where $R^1$, $R^2$, and $R^3$ are each, independently, an alkyl group as described above. A non-limiting example of such a compound is bis(ethylazide) methylamine. The organic azides referred to herein have, in each case, a carbon atom bound directly to one of the nitrogen atoms of the azide ($N_3$) group. Hence, in some cases, it may be more appropriate to refer to the alkyl groups as "alkylenyl" groups.

As illustrated in FIG. 1, for example, dibenzocyclooctynes 2 can be generated by the photo-induced decarbonylation reaction of the corresponding cyclopropenones 1. The dibenzocyclooctynes 2 can then undergo facile reactions with azides preferably to produce quantitative yields of a corresponding triazole 3. It is contemplated that a wide variety of substituents ($R^1$, $R^2$, etc) can be introduced into the aromatic rings of 1 to serve as linkers to substrates of interest, or remain as a substrate of interest themselves. It is contemplated, however, that a preferred group $R^1$ can be either a hydroxyl or an alkoxy group, and in certain embodiments, any substituent linked to an aromatic ring of the dibenzocyclooctyne or dibenzocyclooctyne precursor is not a strong electron withdrawing group such as, but not limited to, a nitro group, a carbonyl group, and a cyano group. It is further contemplated that for certain embodiments, a bulky group ($R^2$) is not linked to a position on an aromatic ring of the dibenzocyclooctyne or dibenzocyclooctyne precursor that is ortho to an alkyne or cyclopropenone substituent of the aromatic ring.

Thus, the method of the present disclosure is a two-step procedure where the "click chemistry' that allows the conjugation of the cyclic alkyne (e.g., a cyclooctyne) with an azide is preceded by the light-inducible formation of the cyclic alkyne, which provides a selective means of initiating the overall pathway, under conditions conducive to their use in living cells without toxic effects from such as cuprous catalysts. The term "click chemistry," as used herein, refers to the Huisgen cycloaddition or the 2,3-dipolar cycloaddition between an azide and a terminal alkyne to form a 1,2,4-triazole. Such chemical reactions can use, but are not limited to, simple heteroatomic organic reactants and are reliable, selective, stereospecific, and exothermic. In the embodiments of the methods encompassed by the present disclosure, the conversion of a cyclopropenone to a cyclic alkyne can be induced by a light source such as, but not limited to, a laser light having a wavelength of from about 220 nm to about 450 nm or even longer (e.g., 350 nm, 405 nm, and 425 nm), from about 325 nm to about 375 nm, from about 325 nm to about 355 nm, and from about 350 nm to about 355 nm. Use of light (laser or non-laser) with a wavelength from about 340 nm to about 375 nm, for example, is desirable when such as dibenzocyclooctyne or the triazole do not absorb light at these wavelengths. The light-inducible reaction, therefore, provides for initiating or triggering the reaction when desired, and focusing of the laser light may allow triggering of the reaction, and therefore the coupling between the cyclopropenone and the azide, at a specific and confined location, such as, for example, a single cell, or at a previously selected location within a cell.

The present disclosure, therefore, provides embodiments of a method of photochemically inducing the ligation of two molecules, the method including: (a) photochemically generating a cyclic alkyne (e.g., cyclooctyne) from a cyclopropenone; and (b) contacting the cyclic alkyne with an azide under conditions effective to form a triazole.

In the embodiments of the methods of the present disclosure, the cyclopropenone may be a dibenzocyclopropenone having the formula I:

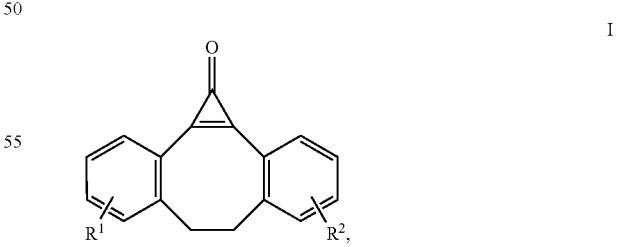

where $R^1$ can be selected from the group consisting of: an alkoxy and a hydroxyl, and $R^2$ can be a substituent, and where, when the cyclooctyne is a dibenzocyclooctyne, $R^2$ is selected from the group consisting of: an alkyl, a heteroalkyl, a cycloalkyl, a heterocycloalkyl, an aryl, an alkoxy, a carboxy, a hydroxyl, an ether, an ester, and a halogen. Alternatively, or in addition to, $R^2$ can be a PEGylated group, a biotinylated group, and/or a group containing an amide or carbamate linker. The cyclooctyne can be a dibenzocyclooctyne.

In these embodiments of the disclosure, $R^1$ and $R^2$ can each be independently linked to any available position of an aromatic ring of the dibenzocyclooctyne or dibenzocyclooctyne precursor.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL's ENCYCLOPEDIA OF PRACTICAL ORGANIC CHEMISTRY 5.sup.TH ED., Longman Scientific and Technical Ltd., Essex, 1991, pp. 809-816; and Heller, Acc. Chem. Res. 23: 128 (1990).

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present disclosure contain between about one and about twenty five carbon atoms (e.g., methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The term "amino" or "amine group" refers to the group —NR'R" (or NRR'R") where R, R' and R" are independently selected from the group consisting of hydrogen, alkyl, substituted alkyl, aryl, substituted aryl, arylalkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, including the group —NRR'R" and its biologically compatible anionic counterions.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsulfonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The terms "alkoxy," "alkylamino", and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, S, and Se, and wherein the nitrogen, phosphorous, sulfur, and selenium atoms are optionally oxidized, and the nitrogen heteroatom is optionally be quaternized. The heteroatom(s) O, N, P, S, Si, and Se may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic group that can be a single ring or multiple rings (preferably from 1 to 3 rings), which are fused together or linked covalently. The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "allyl group substituents," and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R''', —OC(O)R', —C(O)R', —CO2R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound includes more than one R group, for example, each of the R groups is independently selected as are each R', R", R''' and R'''' groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')q-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)r-B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')s-X—(CR"R''')d-, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C1-C6)alkyl.

As used herein, the term "heteroatom" includes oxygen (O), nitrogen (N), sulfur (S), phosphorus (P), silicon (Si), and selenium (Se).

The term "amino" or "amine group" refers to the group —NR'R" (or N⁺RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, including the group —N⁺RR'R" and its biologically compatible anionic counterions.

The term "carboxyalkyl" as used herein refers to a group having the general formula —(CH$_2$)$_n$COOH, where n is 1-18.

The term "linking group" is broadly used herein to refer to any organic (e.g., hydrocarbon) or inorganic (e.g., N, P, O) group that can be used for attaching another group (e.g., a substrate or tag).

In embodiments of the disclosure, the azide or the cyclic alkyne (e.g., a cyclooctyne) may be bound to the surface of a substrate. In these embodiments, the substrate may be a solid substrate or a cell membrane. In other embodiments, the azide or the cyclic alkyne may be integrated into a substrate layer.

In these embodiments, if the azide is bound to the surface of a substrate or integrated into a substrate layer, then the cyclic alkyne (e.g., a cyclooctyne) is a ligand that binds to the azide; and wherein, if the cyclic alkyne is bound to the surface of a substrate or integrated into a substrate layer, then the azide is a ligand that binds to the cyclic alkyne.

In another embodiment of the disclosure, the azide ligand or the cyclic alkyne ligand (e.g., a cyclooctyne) is a detectable label.

In some embodiments of the method of the disclosure, in the cyclopropenone of formula I, R¹ may be a butoxy group and R² may be selected from the group consisting of the formulae:

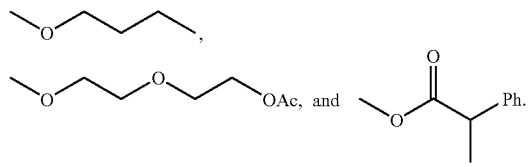

In some other embodiments of the method of the disclosure, in the cyclopropenone of formula I, R¹ may be a butoxy group and R² may be a PEGylated or biotinylated group. In certain embodiments, the biotinylated group has the formula:

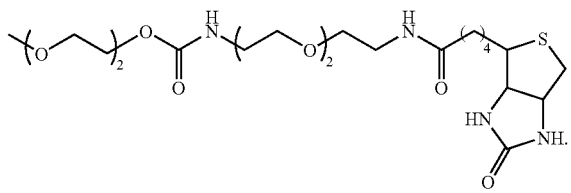

In other embodiments of the method of the disclosure, the cyclopropenone may have the formula II:

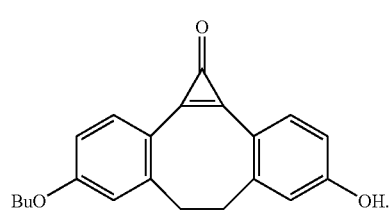

In the embodiments of the method of the disclosure, the azide may be selected from the group consisting of an alkyl azide, a heteroalkyl azide, a cycloalkyl azide, a heterocycloalkyl azide, an alkylamino azide, a benzyl azide, an aryl azide an alkylacyl azide, and an arylacyl azide.

In embodiments of the method of the present disclosure, step (a) includes irradiating the cyclopropenone with light having a wavelength selectively absorbed by the cyclopropenone, and substantially not absorbed by a cyclic alkyne (e.g., a cyclooctyne) or by a triazole. The term "substantially not absorbed" as used herein refers to the degree to which a wavelength, or range of wavelengths, of light is absorbed by one compound when compared with another compound. In particular, the term "substantially not absorbed" as used in the embodiments of the present disclosure, therefore, indicates that a cyclic alkyne or triazole will absorb less than about 20%, advantageously less than about 10%, more advantageously less than about 5%, and most advantageously about 0% of the light absorbed by a cyclopropenone that has a wavelength able to initiate the conversion of the cyclopropenone to a cyclic alkyne.

In the embodiments of the methods encompassed by the present disclosure, the wavelength of light is from about 220 nm to about 450 nm or even longer (e.g., 350 nm, 405 nm, and 425 nm). In certain embodiments of the disclosure, the wavelength of light may be from about 325 nm to about 375 nm. In other embodiments, the wavelength of light may be from about 325 nm to about 360 nm. In yet other embodiments, the wavelength of light may be from about 350 nm to about 355 nm. In still other embodiments, the wavelength of light may be from about 340 nm to about 355 nm.

In embodiments of the method of the present disclosure, the method may further include the step of providing a cyclooctyne, said step including: (i) providing a 3,3'-dialkyloxybibenzyl; and (ii) reacting the 3,3'-dialkyloxybibenzyl with tetrachloropenone in the presence of anhydrous aluminum chloride under medium dilution conditions effective to form a cyclopropenone.

In one embodiment of the method of the disclosure, the 3,3'-dialkyloxybibenzyl is 3,3'-dibutoxybibenzyl, and the cyclopropenone has the formula I:

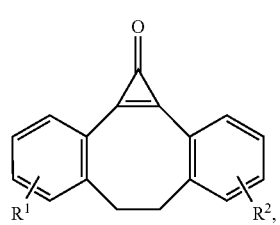

where $R^1$ is selected from the group consisting of: an alkoxy and a hydroxyl, and $R^2$ is a substituent. In these embodiments of the methods of the disclosure, $R^2$ may be selected from the group consisting of: an alkyl, a heteroalkyl, a cycloalkyl, a heterocycloalkyl, an aryl, an alkoxy, a carboxy, a hydroxyl, an ether, an ester, and a halogen. Alternatively, or in addition to, $R^2$ can be a PEGylated group, a biotinylated group, and/or a group containing an amide or carbamate linker.

In some embodiments of the method of the disclosure, the yield of the reaction in step (ii) may include a compound having the formula II and a compound having the formula III:

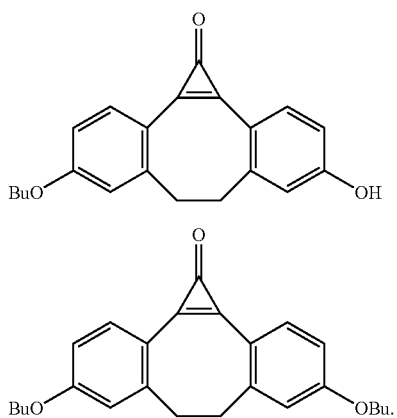

In certain embodiments of the method of the disclosure, the azide may have the formula:

where $R^3$ may be selected from the group consisting of an alkyl, a heteroalkyl, a cycloalkyl, a heterocycloalkyl, an alkylamino, an aryl, an alkylacyl, and an arylacyl.

In certain embodiments of the method of the present disclosure, the triazole may have the formula:

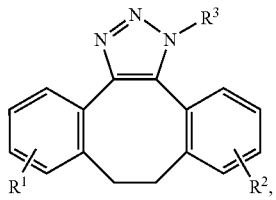

where $R^1$ can be selected from the group consisting of: an alkoxy and a hydroxyl; $R^2$ can be selected from the group consisting of: an alkyl, a heteroalkyl, a cycloalkyl, a heterocycloalkyl, an aryl, an alkoxy, a carboxy, a hydroxyl, an ether, an ester, and a halogen; and wherein $R^3$ can be selected from the group consisting of a primary alkyl, a secondary alkyl, a tertiary alky, an aryl, an alkylaryl, an acyl, an alkylacyl, and an arylacyl.

In some embodiments, $R^2$ may be selected from the group consisting of an alkyl, a heteroalkyl, a cycloalkyl, a heterocycloalkyl, an aryl, an alkoxy, a carboxy, a hydroxyl, an ether, an ester, and a halogen. Alternatively, or in addition to, $R^2$ can be a PEGylated group, a biotinylated group, and/or a group containing an amide or carbamate linker.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

Biomaterials

Figure 2:
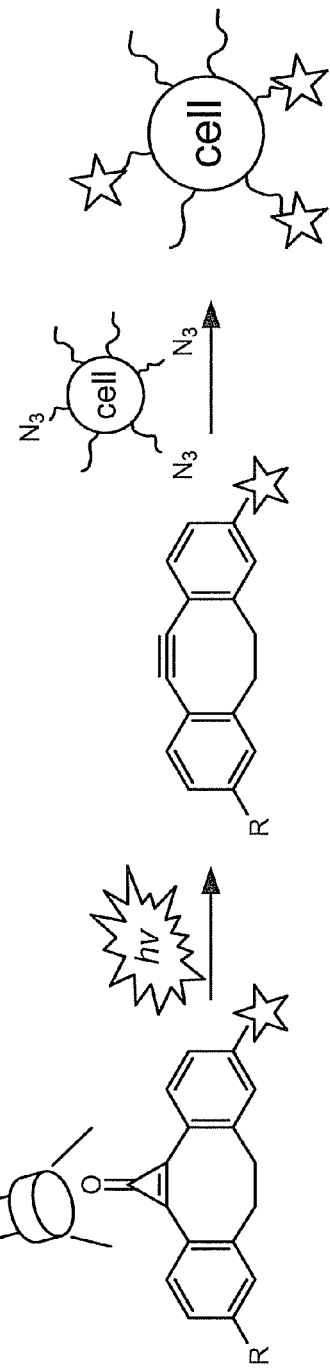
FIG. 2 illustrates an exemplary embodiment in which cyclopropenone-based "photo-click" chemistry can be used to label living organisms.

Photo-triggering of the azide to acetylene cycloaddition reaction (e.g., preferably metal-free) was achieved by masking the triple bond of dibenzocyclooctynes as cyclopropenone. Such masked cyclooctynes do not react with azides in the dark. Irradiation of cyclopropenones results in the efficient ($\Phi_{355}$=0.33) and clean regeneration of the corresponding dibenzocyclooctynes, which then undergo facile cycloadditions (e.g., catalyst-free cycloadditions) with azides to give corresponding triazoles under ambient conditions. In-situ light activation of a cyclopropenone linked to biotin made it possible to label living cells expressing glycoproteins containing N-azidoacetyl-sialic acid. As illustrated in FIG. 2, the cyclopropenone-based "photo-click" chemistry offers exciting opportunities to label living organisms in a temporal and for spatial controlled and may facilitate the preparation of microarrays.

The bioorthogonal chemical reporter strategy is emerging as a versatile method for labeling of biomolecules such as nucleic acids, lipids, proteins, and carbohydrates. In this approach, a unique chemical functionality is incorporated into a targeted biomolecule, preferably by the biosynthetic machinery of the cell, followed by a specific chemical reaction of the functional group with an appropriate probe. In particular, the azide is an attractive chemical reporter because of its small size, diverse mode of reactivity, and bio-orthogonality. Azides can be incorporated into biomolecules using a variety of strategies such as post synthetic modification, in-vitro enzymatic transfer, the use of covalent inhibitors, and metabolic labeling by feeding cells a biosynthetic precursor modified with an azido function.

The most commonly employed bioorthogonal reactions with azides include the Staudinger ligation with phosphines, copper(I)-catalyzed cycloaddition with terminal alkynes, and strain-promoted cycloaddition with cyclooctynes. The latter type of reaction, which was coined copper-free click chemistry, does not require a cytotoxic metal catalyst, which can therefore offer a unique opportunity for labeling living cells. The attraction of this type of technology was elegantly demonstrated by a study of the Bertozzi laboratory in which glycans of the developing zebrafish were imaged using a difluorinated cyclooctynes derivative (e.g., Laughlin et al., *Science* 2008, 320:664-667). Boons and coworkers have demonstrated that derivatives of 4-dibenzocyclooctynol (4a, b; DIBO, FIG. 3) react exceptionally fast in the absence of a $Cu^I$ catalyst with azido-containing saccharides and amino acids, and can be employed for visualizing glycoconjugates of living cells that are metabolically labeled with azido-containing monosaccharides (e.g., Ning et al., *Angew. Chem. Int. Ed.* 2008, 47:2253-2255).

Figure 3:
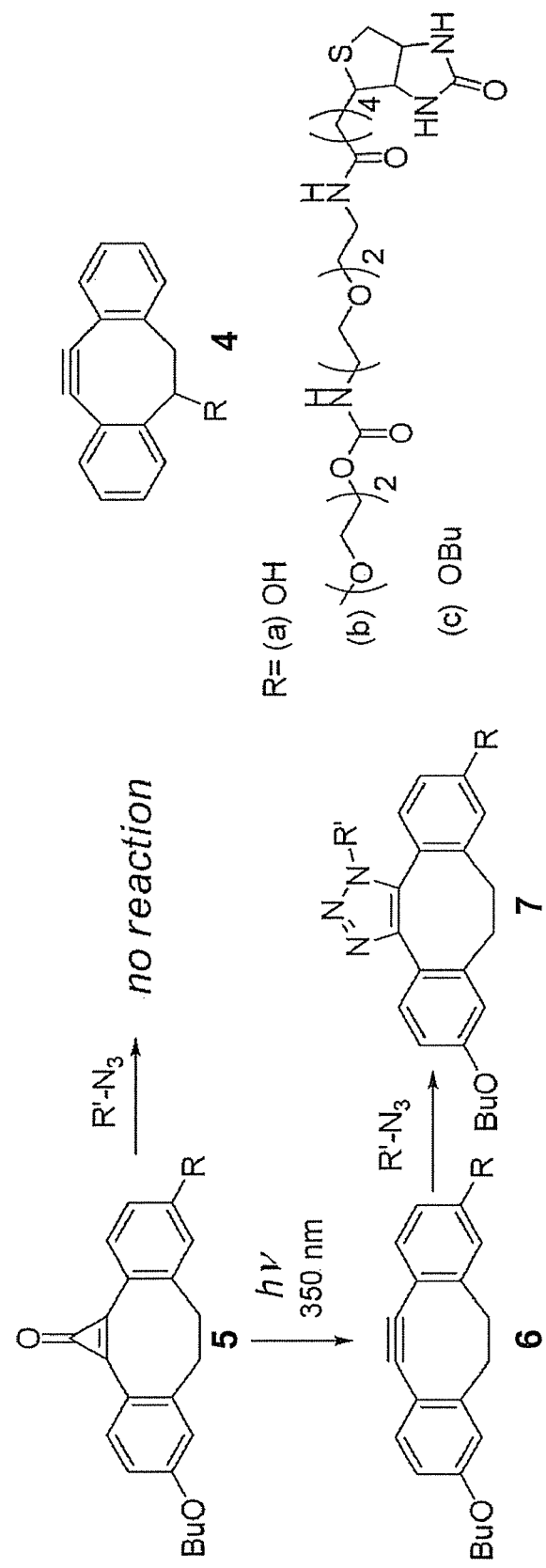
FIG. 3 illustrates a generalized scheme for photochemical initiation of a acetylene-azide cycloaddition, preferably without the use of a copper catalyst.

The utility of azide-based bioorthogonal reporter strategy can be further extended by the development of a photochemically-triggered click reaction, as this approach allows for the spatial and temporal control of the labeling of the target substrates. In fact, photochemical release or generation of an active molecule is widely employed strategy to deliver bioactive compounds to small, addressable target sites in a time-controlled manner (e.g., Pelliccioli et al., *Photochem. Photobiol. Sci.* 2002, 1:441-458; Mayer et al., *Angew. Chem. Int. Ed.* 2006, 45:4900-4921; Ellis-Davies, *Nat. Methods* 2007, 4:619-628; and Song et al., *J. Am. Chem. Soc.* 2008, 130: 9654-9655). To achieve this goal, we have explored photochemical generation of reactive dibenzocyclooctynes. It is known that single (e.g., Kuzmanich et al., *J. Am. Chem. Soc.* 2008, 130:1140-1141; Chiang et al., *J. Phys. Org. Chem.* 1996, 9:361-370; Dehmlow et al., *Chem. Ber.* 1988, 121:569; Murata et al., *J. Am. Chem. Soc.* 1993, 115:4013-4023; Chapman et al., *J. Am. Chem. Soc.* 1981, 103, 7033-7036; and Poloukhtine et al., *J. Org. Chem.* 2003, 68:7833-7840) or two-photon (e.g., Urdabayev et al., *Chem. Commun.* 2006, 454-456) excitation of cyclopropenones results in the formation of corresponding acetylenes. Photochemical decarbonylation of thermally stable diaryl-substituted cyclopropenones is especially efficient ($\Phi$=0.6-1.0) and produces alkynes in a quantitative yield (e.g., Poloukhtine et al., *J. Org. Chem.* 2003, 68:7833-7840). This reaction is also extremely fast and is complete within few hundred picoseconds after excitation (e.g., Poloukhtine et al., *J. Phys. Chem. A* 2006, 110:1749-1757). We have already employed cyclopropenone groups in the development of photoswitchable enediynes (e.g., Poloukhtine et al., *Chem. Commun.* 2005, 617-619; Poloukhtine et al., *J. Org. Chem.* 2005, 70:1297-1305; Poloukhtine et al., *J. Org. Chem.* 2006, 71:7417-7421; and Pandithavidana et al., *J. Am. Chem. Soc.* 2009, 131:351-356). Here we report a novel "photo-click" strategy for the ligation of azides, which in preferred embodiments is metal-free (FIG. 3). Cyclopropenones, such as 5, do not react with azides under ambient conditions in the dark but efficiently produce reactive dibenzocyclooctynes 6 upon irradiation. The latter type of compound could be employed for labeling of living cells modified with azido-containing cell surface saccharides.

Interestingly, the rate constants for cycloaddition of acetylene 6a-c with benzyl- and phenyl azide at 25±0.1° C. were very similar to that of dibenzocyclooctynol (4a) (e.g., Ning et al., *Angew. Chem. Int. Ed.* 2008, 47:2253-2255), and thus, the aromatic alkoxy-substitutents of 6a-c do not appear to influence the rate constants (6c: PhN$_3$ 0.0163±0.0006 M$^{-1}$s$^{-1}$; BnN$_3$ 0.0763±0.0011 M$^{-1}$s$^{-1}$; 4a: 0.0567±0.0027 M$^{-1}$s$^{-1}$ and 0.17 M$^{-1}$s$^{-1}$) (e.g., Ning et al., *Angew. Chem. Int. Ed.* 2008, 47:2253-2255).

Synthesis of Cyclopropenones 5a-c and Acetylene 6b.

Friedel-Crafts alkylation of appropriate substrates with tricholorocyclopropenium cation followed by a controlled hydrolysis of the resulting dichlorocyclopropene offers a convenient synthesis of aromatic cyclopropenones (e.g., Poloukhtine et al., *J. Org. Chem.* 2003, 68:7833-7840). Thus, the target cyclopropenone 5a was obtained by treatment of 3,3'-bisbutoxybibenzyl (8) with tetrachlorocyclopene in the presence of aluminum chloride followed by in situ hydrolysis of the intermediate dichlorocyclopropene. In addition to 5a, a small amount of a bis-butoxy analog (5c) was isolated (FIG. 4) (see Examples).

Figure 4:
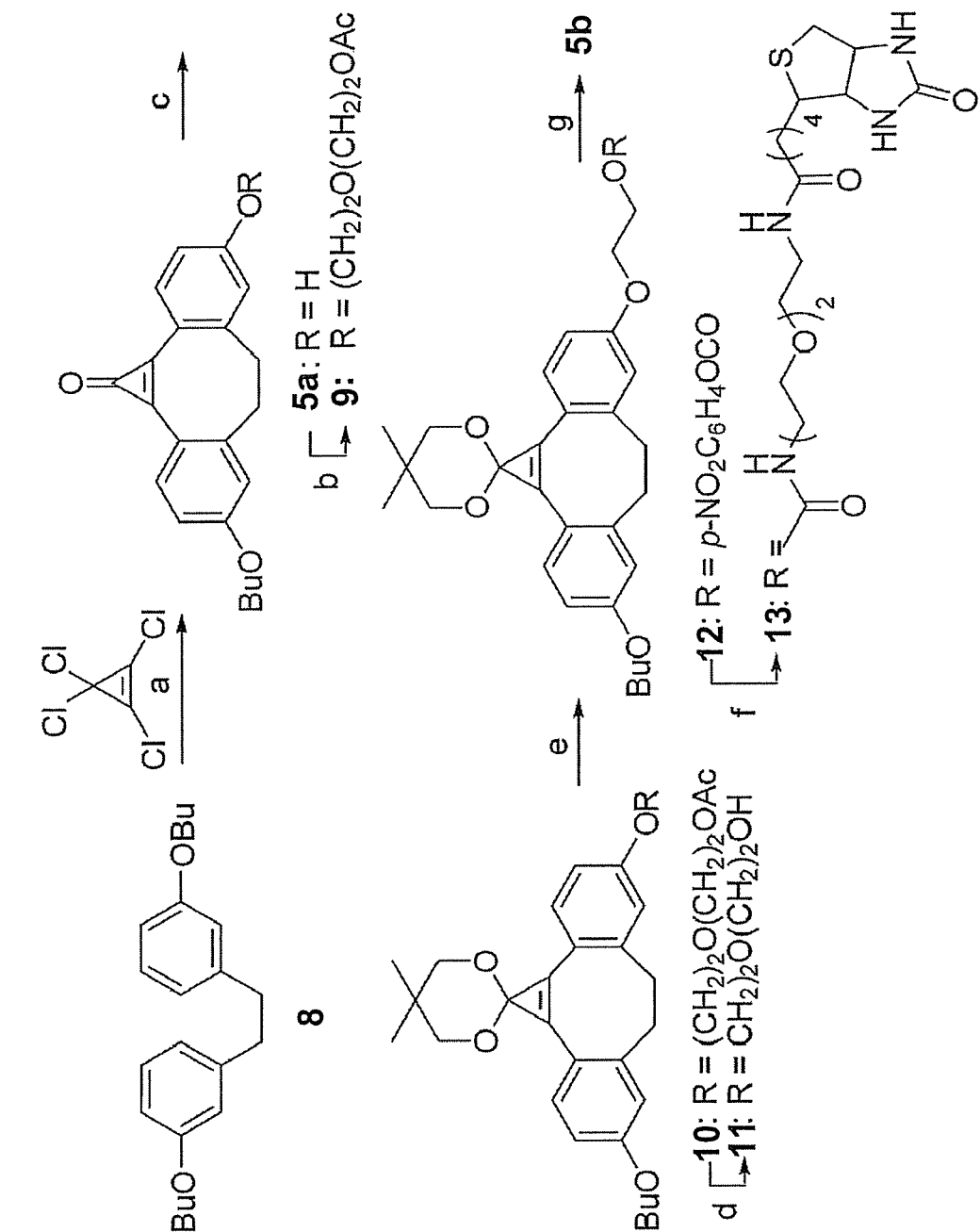
FIG. 4 illustrates a generalized scheme for the preparation of various cyclopropenones. Reagents and conditions: a) AlCl$_3$; b) HO(CH$_2$)$_2$O(CH$_2$)$_2$OAc, PPh$_3$, DEAD, THF; c) neopentyl glycol, BF$_4$O(C$_2$H$_5$)$_3$, Et$_3$N, CH$_2$Cl$_2$; d) NaOH, MeOH; e) p-nitrophenyl chloroformate, pyridine; f) N-Boc-N'-biotinyl-3,6-dioxaoctane-1,8-diamine, Et$_3$N, DMF; g) Amberyst-15 H$^+$, acetone.
Figure 5:
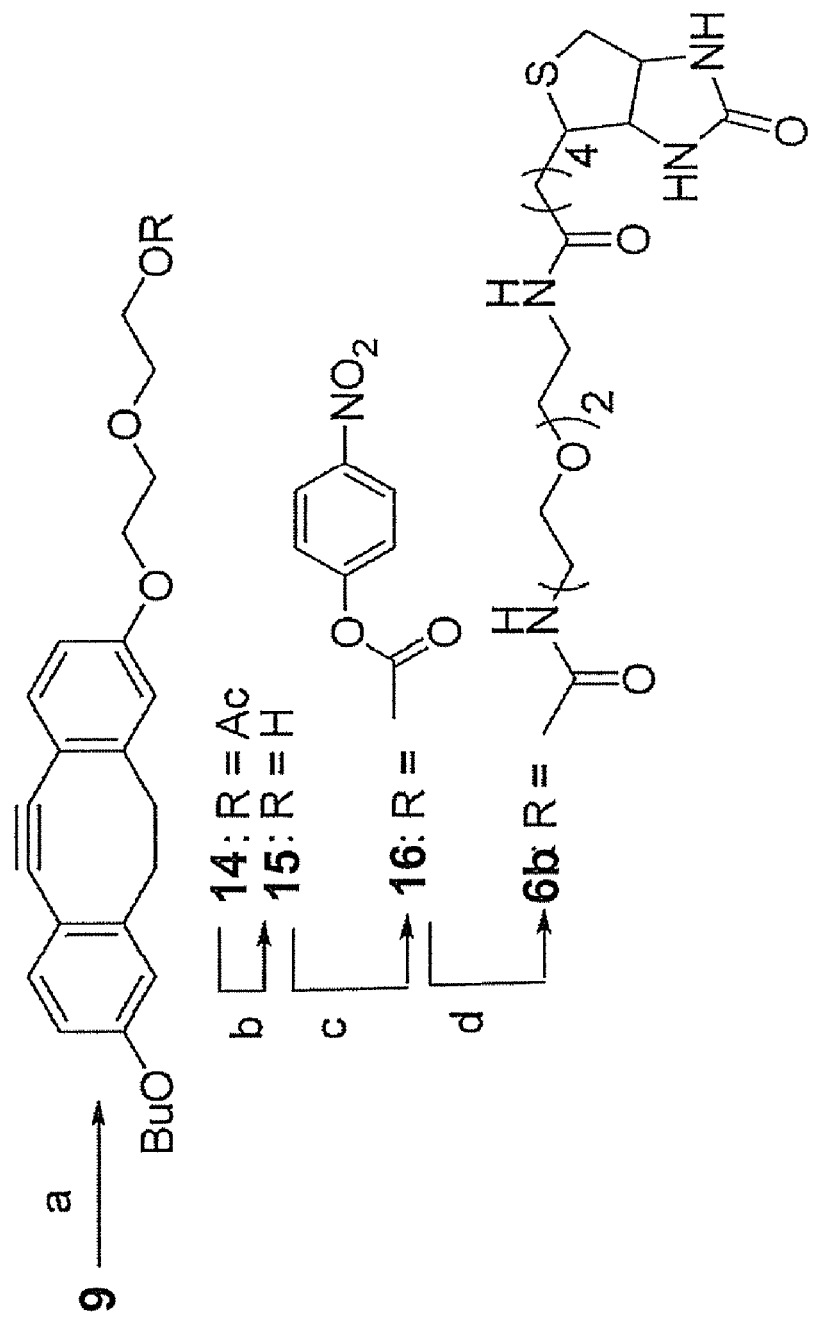
FIG. 5 illustrates an independent preparation of biotinylated acetylene 6b. Reagents and conditions. a) 350 nm irradiation, MeOH-THF; b) NaOH, MeOH; c) p-nitrophenyl chloroformate, pyridine; d) N-Boc-N'-biotinyl-3,6-dioxaoctane-1,8-diamine, Et$_3$N, DMF.

To explore the utility of the "photo-click" chemistry for the temporal and spatial controlled labeling of live cells, we have prepared the biotinylated cyclopropenone 5b (FIG. 4). Thus, cyclopropenone 5a was coupled with diethylene glycol acetate under Mitsunobu conditions to give 9 in 92% yield. The carbonyl group of cyclopropenone 9 was protected as a neopentyl glycol acetal by treatment with neopentyl glycol in the presence of BF$_4$O(C$_2$H$_5$)$_3$ and the acetyl ester of the resulting compound 10 was saponified with sodium methoxide in methanol to produce 11. Treatment of 10 with 4-nitrophenyl chloroformate gave activated intermediate 12, which was immediately reacted with N-Boc-N'-biotinyl-3,6-dioxaoctane-1,8-diamine to provide carbamate 13. Finally, the acetal-protecting group of 13 was removed to give the required cyclopropenone-biotin conjugate 5b by the treatment with Amberlyst 15 in acetone. The performance of the "photo-click" reagent 5b was compared to a known labeling reagent 4b and to the independently prepared biotinylated dibenzocyclooctyne 6b (FIG. 5).

Dibenzocyclooctyne 14 was synthesized by the preparative photolysis of cyclopropenone 9. Conjugation of the former with a biotin group followed procedures used in the conversion of acetal 10 into compound 13 (FIG. 4).

The UV spectra of methanol solutions of cyclopropenones 5a-c contain two close-lying intense bands ($\lambda_{max}$=331 nm and 347 nm, logs approximately 4.5, FIG. 6) (see Examples). Irradiation of 5a-c with 350 nm light resulted in efficient ($\Phi_{355}$=0.33) decarbonylation of the starting material, which can be observed by bleaching of the 331-347 nm bands, and the quantitative formation of acetylenes 6a-c. Incubation of solutions of cyclopropenone 5a-c and benzyl- or phenyl azide in the dark for several days did not result in detectable changes in UV absorbance. HPLC analysis of the mixture showed only the presence of starting materials. Upon irradiation of these solutions, however, the azides rapidly reacted with photo-generated cycloalkyne 6a-c to produce the corresponding triazoles 7a-c in quantitative yields. It should be noted that the photoproducts 6a-c and 7a-c have virtually no absorbance above 340 nm (FIG. 6; see Examples), thus allowing for selective irradiation of cyclopropenones 5a-c in their presence and for the convenient monitoring of the reaction progress.

Kinetics of the cycloaddition reaction. The rate measurements of cycloaddition of acetylenes 6c and 4a were conducted by UV spectroscopy at 25±0.1° C. A calculated amount of 0.25 M solutions of an azide required to achieve desired azide concentration (6×10$^{-4}$-1.5×10$^{-2}$M) was added to a thermally equilibrated ca. 6×10$^{-5}$ M solution of acetylene in MeOH. Reactions were monitored by following the decay of the characteristic absorbance of acetylenes ca. 317 nm (FIG. 6). Consumption of starting material followed a first order equation well and the pseudo-first order rate constants were obtained by the by least-squares fitting of the data to a single exponential equation. The dependence of the observed rates on the concentration of azides was linear. The least-squares fitting of the data to a linear equation produced bimolecular rate constants summarized in Table 2. It was found that this method provides is more accurate values of rate constant compared to that determination by NMR. Interestingly, the rate constants for cycloaddition of acetylene 6c with benzyl azide were very similar to that of dibenzocyclooctynol (4a), and thus, the aromatic alkoxy-substitutents of 6a-c do not appear to influence the rate constants.

TABLE 2

Bimolecular rate constants for the reaction of acetylene 4a and 6c with azides in methanol

| Acetylene | Azide | Rate (M$^{-1}$ s$^{-1}$) |
| --- | --- | --- |
| 4a | Benzyl azide | 5.67 × 10$^{-2}$ |
| 6c | Benzyl azide | 7.63 × 10$^{-2}$ |
| 6c | n-Butyl azide | 5.86 × 10$^{-2}$ |
| 6c | 1-Phenyl-2-azidopropane | 3.43 × 10$^{-2}$ |
| 6c | Phenyl azide | 1.63 × 10$^{-2}$ |

Figure 7A:
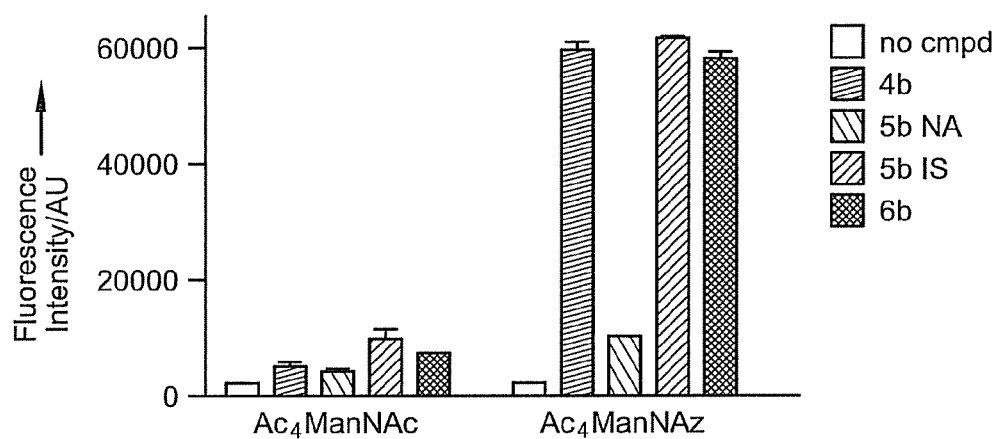
FIG. 7 illustrates cell surface labeling with compounds 4b, 5b, and 6b. Jurkat cells grown for 3 days in the presence of a) Ac$_4$ManNAc (25 micromolar) or a-c) Ac$_4$ManNAz (25 micromolar) were incubated at room temperature with compounds 4b, 5b, and 6b at a) 30 micromolar for 1 hour, b) 0-100 micromolar for 1 hour, or c) 30 micromolar for 0-90 minutes. Compound 5b was assessed without activation (5b NA) and after light activation in situ (1 minute at 350 nm; 5b IS). Next, cells were incubated with avidin-FITC for 15 minutes at 4° C., after which cell lysates were assessed for fluorescence intensity. AU indicates arbitrary fluorescence units.

Having established that light activation of cyclopropenones results in the clean formation of the corresponding dibenzocyclooctynes, which can undergo cycloadditions with azides (e.g., metal-free cycloadditions in preferred embodiments) to give corresponding triazoles, attention was focused on labeling living cell modified with azido groups. Thus, Jurkat cells were cultured in the presence of 25 mM of peracetylated N-azidoacetylmannosamine (Ac$_4$ManNAz)

for 3 days to metabolically introduce N-azidoacetyl-sialic acid (SiaNAz) groups into glycoproteins and glycolipids. As a negative control, Jurkat cells were employed that were grown in the presence of peracetylated N-acetylmannosamine (Ac$_4$ManNAc). The cells were exposed to 30 micromolar of compound 4b, 5b, and 6b for 1 hour at room temperature. In addition, cells and cyclopropenone 5b were exposed to light (350 nm) for 1 minute to form in-situ cyclooctyne 6b and then incubated for 1 hour at room temperature. Next, the cells were washed and stained with avidin-fluorescein isothiocyanate (FITC) for 15 minutes at 4° C. The efficiency of the two-step cell surface labeling was determined by measuring the fluorescence intensity of the cell lysates. Cyclooctynes 4b and 6b exhibited strong labeling of the cells (FIG. 7a). Furthermore, in-situ activation of 5b to give 6b resulted in equally efficient cell labeling. As expected, low fluorescence intensities were measured when cells were exposed to cyclopropenone 5b in the dark demonstrating that this compound can be selectively activated by a short irradiation with 350 nm light. Corresponding control cells showed negligible background labeling.

Figure 7B:
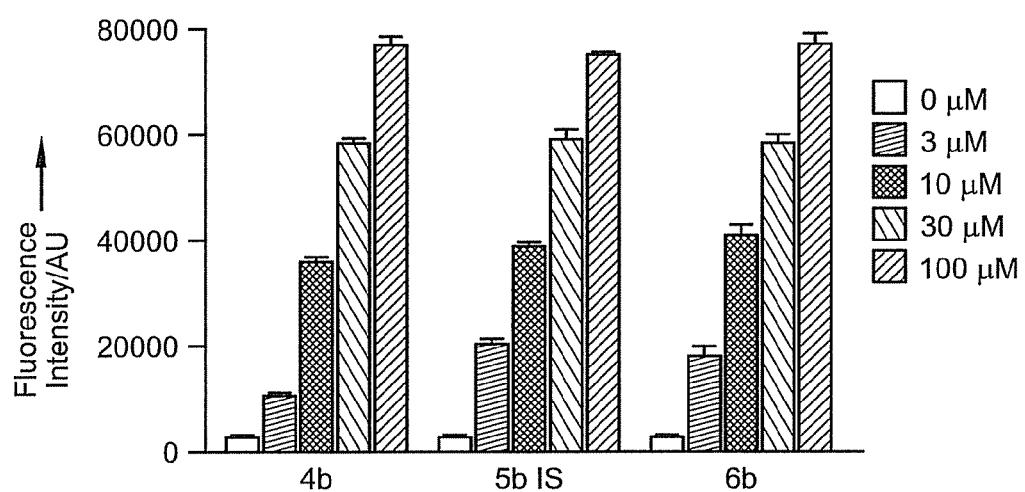

The concentration-dependency of the cell surface labeling was studied by incubating cells with various concentrations of 4b, in-situ activated 5b, and 6b, followed by staining with avidin-FTIC (FIG. 7b).

Jurkat cells were cultured in the presence of 25 mM of peracetylated N-azidoacetylmannosamine (Ac$_4$ManNAz) for 3 days to metabolically introduce N-azidoacetyl-sialic acid (SiaNAz) groups into glycoproteins. As a negative control, Jurkat cells were employed that were grown in the presence of peracetylated N-acetylmannosamine (Ac$_4$ManNAc). The cells were exposed to 30 micromoles of compound 4b, 5b, and 6b for 1 hour at 37° C. In addition, cells and cyclopropenone 5b were exposed to light (350 nm) for 1 minute to form in-situ cyclooctyne 6b and then incubated for 1 hour at 37° C. Next, the cells were washed and stained with avidin-fluorescein isothiocyanate (FITC) for 15 minutes at 4° C. and the efficiency of the two-step cell surface labeling was determined by measuring the fluorescence intensity of the cell lysates. Cyclooctynes 4b and 5b exhibited strong labeling of the cells (FIG. 7a). Furthermore, in-situ activation of 5b to give 6b resulted in equally efficient cell labeling. As expected, low fluorescence intensities were measured when cells were exposed to cyclopropenone 5b in the dark demonstrating that this compound can be selectively activated by a short irradiation with 350 nm light. Corresponding control cells showed negligible background labeling. To ensure that light activation of 5b had no effect on cell viability, cell morphology and exclusion of trypan blue were examined after exposure to UV light for 1 minute and fortunately no changes were observed compared to cells that were not exposed to UV light (data not shown).

Figure 7C:
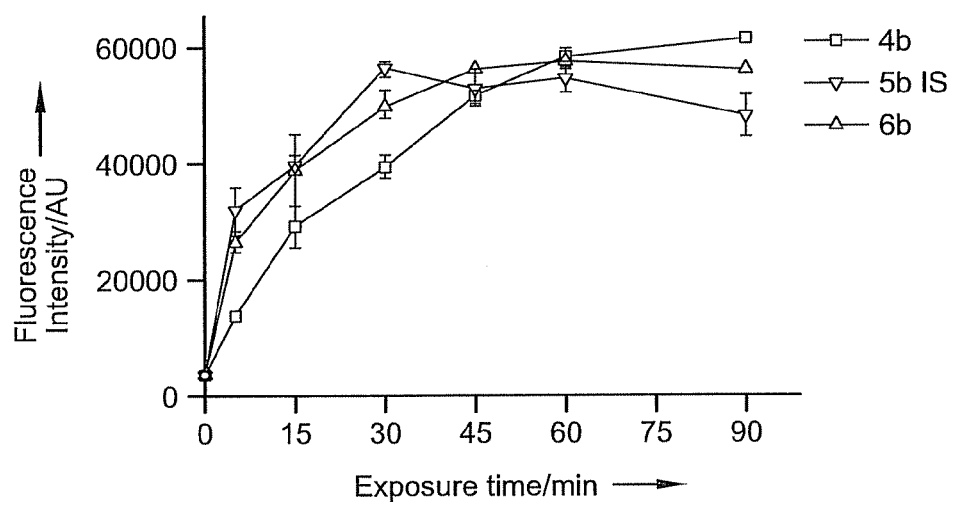

The concentration-dependency of the cell surface labeling was studied by incubation cells with various concentrations of 4b, in-situ activated 5b, and 6b, followed by staining with avidin-FTIC (FIG. 7b). As expected, cells displaying azido groups showed a dose-dependent increase in fluorescence intensity. Reliable fluorescent labeling was achieved at a concentration of 3 micromolar, however, optimal results were obtained at concentrations ranging from 10 to 100 micromolar. Interestingly, at low concentration 6b gave a somewhat higher fluorescent reading than 4b. A time course experiment demonstrated that the labeling with 4b and 6b was reaching completion at an incubation time of 60 minutes (FIG. 7c).

Figure 8:
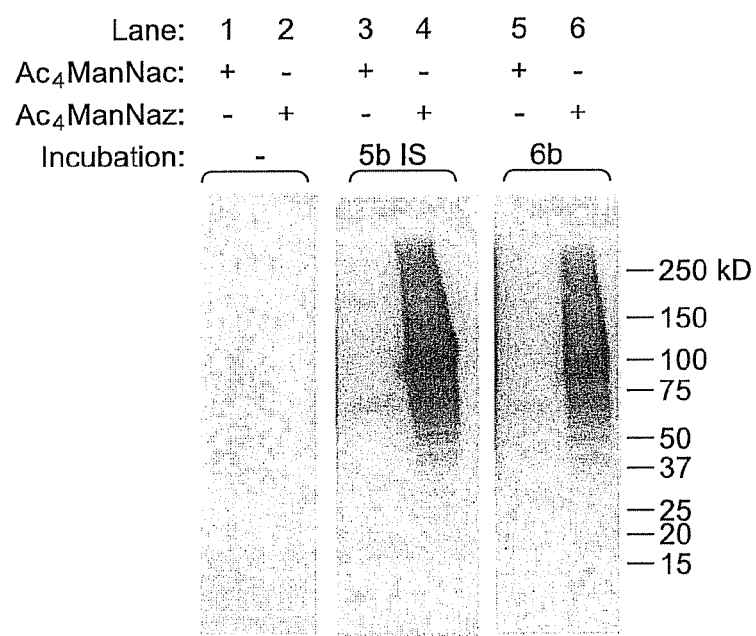
FIG. 8 illustrates a Western blot analysis of cell surface labeling with compounds 5b and 6b. Jurkat cells grown for 3 days in the presence of $Ac_4ManNAc$ (25 micromolar; lanes 1, 3, and 5) or $Ac_4ManNAz$ (25 micromolar; lanes 2, 4, and 6) were incubated with 5b (lanes 3 and 4), 6b (lanes 5 and 6) (30 micromolar), or without compound (lanes 1 and 2) for 1 hour at room temperature. Compound 5b was assessed after light activation in situ (5b IS). Cell lysates (20 micrograms total protein per lane) were resolved by SDS-PAGE and the blot was probed with an anti-biotin antibody conjugated to HRP. Total protein loading was confirmed by Coomassie staining of the gel (not shown).

To identify the nature of the azide-labeled Jurkat glycoconjugates, cell lysates were analyzed by Western blot analysis (FIG. 8). Jurkat cells grown for 3 days in the presence of Ac$_4$ManNAc or Ac$_4$ManNAz were incubated with compounds in-situ activated 5b or 6b (30 micromolar) and then lysed. The Western blot was probed with an anti-biotin antibody conjugated to horseradish peroxidase (HRP). Significant glycoprotein labeling was only observed in lysates from cells grown in the presence of Ac$_4$ManNAz. Furthermore, similar patterns of labeling were apparent after incubation with in-situ activated 5b and 6b.

Figure 9:
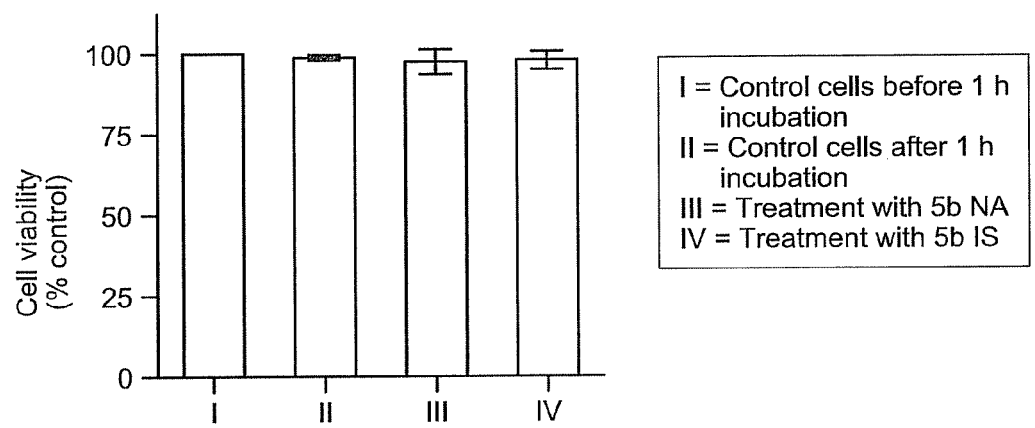
FIG. 9 is a graph illustrating a toxicity assessment of cycloaddition reaction with compound 5b. Jurkat cells grown for 3 days in the presence of $Ac_4ManNAz$ (25 micromolar) were incubated with compound 5b (30 micromolar) for 1 hour at room temperature. Cell viability after incubation with 5b was assessed without activation (5b NA; III) and after light activation in situ (1 minute at 350 nm; 5b IS; IV). Control cells were treated similarly, but without exposure to 5b and UV light (II). Cell viability was assessed with trypan blue exclusion. Cell viability values were normalized for the amount of viable cells of the sample with control cells before the incubation period (100%; I).

To ensure that in situ activation of 5b had no effect on cell viability and morphology, cells were assessed for the ability to exclude trypan blue and fortunately no changes were observed compared to cells that were not exposed to 5b both with and without UV light activation (FIG. 9). Cell viability was also examined after incubation with 5b with and without light activation followed by reincubation for 5 hours (see Examples). In both cases, the ability of the cells to reduce MTT to its insoluble formazan salt was negligible.

Figure 10:
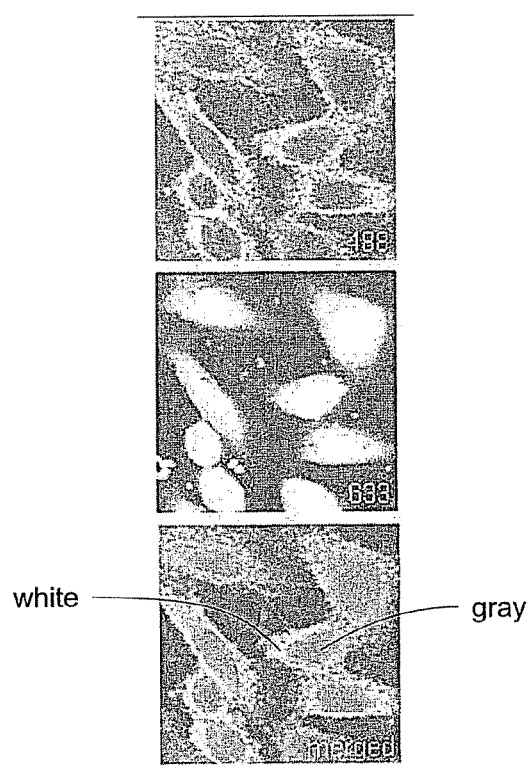
FIG. 10 illustrates exemplary fluorescence images of cells labeled with compound 5b and avidin-Alexa fluor 488. CHO cells grown for 3 days in the presence of $Ac_4ManNAc$ (100 micromolar; A) or $Ac_4ManNAz$ (100 micromolar; B) were given compound 5b (30 micromolar), subjected to 1 minute of UV light for in situ activation (5b IS), and further incubated for 1 hour at room temperature. Next, cells were incubated with avidin-Alexa Fluor 488 for 15 minutes at 4° C. and, after washing, fixing, and staining for the nucleus with the far-red-fluorescent dye TO-PRO-3 iodide, imaged. Merged indicate that the images of cells labeled with Alexa Fluor (488 nm) and TO-PRO iodide (633 nm) are merged and shown in white and gray, respectively.

Next, attention was focused on visualizing azido-containing glycoconjugates of living cells by confocal microscopy. Thus, adherent Chinese hamster ovary (CHO) cells were cultured in the presence of Ac$_4$ManNAz (100 µM) for three days. The resulting cell surface azido groups were reacted with in situ generated 6b (30 µM) and then visualized with avidin-Alexa fluor 488. As expected, staining was only observed at the cell surface (FIG. 10) and showed similar cell surface labeling as obtained by staining with 4b. Cells cultured in the presence of Ac$_4$ManNAz (100 µM) exhibited very low fluorescence staining, confirming that background labeling is negligible. As expected, cells metabolically labeled with ManNAz and exposed to 5b in the dark showed also negligible staining.

In conclusion, it has been shown that light activation of cyclopropenone 5a-c results in the clean formation of the corresponding dibenzocyclooctyne 6a-c, which can undergo fast cycloadditions (e.g., catalyst-free cycloadditions) with azides to give corresponding triazoles. In-situ light activation of 5b made it possible to efficiently label living cells expressing glycoproteins containing N-azidoacetyl-sialic acid. The cyclopropenone-based "photo-click" chemistry reported here can provide greater bioorthogonality and versatility than recently developed reaction of alkenes with a photo-generated nitrile imine (e.g., Song et al., *J. Am. Chem. Soc.* 2008, 130:9654-9655). It is to be expected that the properties of compounds such as 5b will make it possible to label living organisms in a temporal and spatial controlled manner (e.g., Pelliccioli et al., *Photochem. Photobiol. Sci.* 2002, 1:441-458; Mayer et al., *Angew. Chem. Int. Ed.* 2006, 45:4900-4921; and Ellis-Davies, *Nat. Methods* 2007, 4:619-628). Furthermore, the hydroxy group in 5a can be easily esterified or converted to an ether (e.g., 9) thus allowing for the attachment of the "photo-click" group to various substrates or surfaces. Compounds derived from 5a can offer opportunities for temporal and spatial controlled ligation (e.g., copper-free ligation in preferred embodiments), which may for example be attractive for microarray development. In addition to this type of application, it is to be expected that other fields of science such the fabrication of microarrays and the preparation of multifunctional materials, may benefit from photo-click chemistry. In this respect, Cu-mediated click reactions have been used for the fabrication of saccharide microarrays by offering a convening approach to immobilize azide-modified saccharides to an alkyne-modified surface (e.g., Sun et al., *Bioconjugate Chem.* 2006, 17:52). It is to be expected that surface modification with compounds 5a will offer an exciting opportunities for spatially controlled ligand immobilization using light activation followed by ligation (e.g., copper-free ligation in preferred embodiments). Furthermore, metal-free click reactions have been applied in materials chemistry (e.g., Johnson et al., *Chem. Com.* 2008, 3064-3066; Lallana et al., *J. Am. Chem. Soc.* 2009, 131:5748; and Inglis et al., *Angew. Chem. Int. Ed. Engl.* 2009, 48:2411-2414), and the obvious advantage of such a synthetic approach is that it offers a reliable approach for macromolecule modification without the need of using toxic reagents. Therefore, it is to be expected that the combined use of traditional- and photo-activated metal click reactions will offer an attractive approach for multi-functionalization of polymers and macromolecules (e.g., Lundberg et al., *Macromol. Rapid Comm.* 2008, 29:998-1015; Lutz, *Angew. Chem. Int. Ed. Engl.* 2007, 46:1018; and Fournier et al., *Chem. Soc. Rev.* 2007, 36:1369-1380).

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere. The term "aqueous solution" as used herein refers to a solution that is predominantly water and retains the solution characteristics of water. Where the aqueous solution contains solvents in addition to water, water is typically the predominant solvent.

EXAMPLES

Example 1

Figure 11:
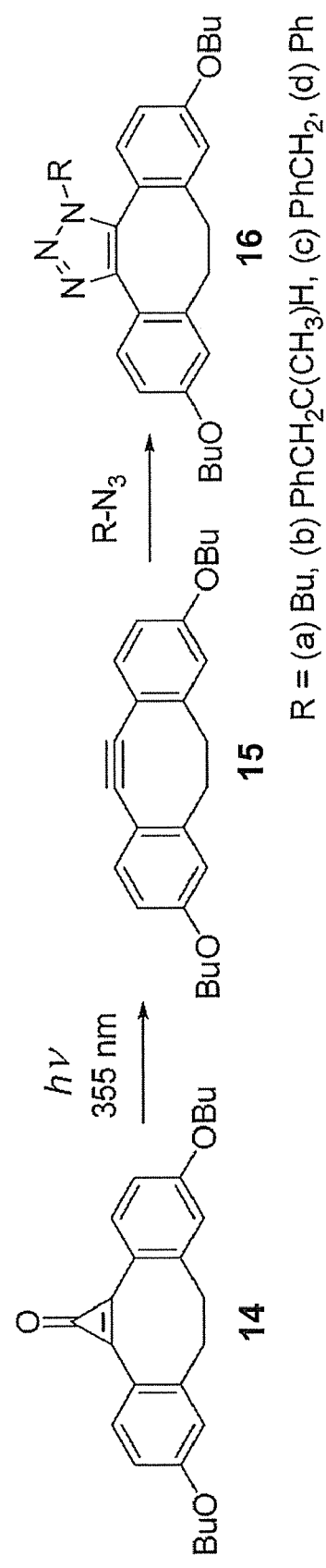
FIG. 11 illustrates a scheme for the synthesis of embodiments of a triazole from a dibenzocyclooctyne, where the R substituent on the triazole is defined.

Photophysical properties, generation, and reactivity of dibenzocyclooctynes. Refer now to FIG. 11, and to FIG. 6. The UV spectrum, as shown in FIG. 6, of cyclopropenone 14 in methanol contained two close-lying bands ($\lambda_{max}$ of about 331 nm and about 347 nm) of similar intensity (logs approximately 4.5; FIG. 6). Irradiation of methanol solutions of 14 with 350 nm (UV lamp) or 355 nm (Nd-YAG laser) light resulted in the efficient ($\Phi_{355}$=0.33) decarbonylation of cyclopropenone 14, and the quantitative formation of the corresponding acetylene 15, as shown in FIG. 11.

The photochemistry is very clean since no additional photoproducts were detected in the photolysates. The acetylene 15 then rapidly reacted with alkyl- or aryl azide present in solution to give the triazole 16. It is important to note that the absorbance bands of the acetylene 15 ($\lambda_{max}$=about 301 and about 317 nm, as shown in FIG. 6), and of the triazole 16 ($\lambda_{max}$=about 310 nm, as shown in FIG. 6) are shifted to the shorter wavelengths, in comparison to the starting material 14. Both the acetylene 15 and triazole 16 have virtually no absorbance above about 340 nm. This feature allows for the selective irradiation of cyclopropenone 14 and for the monitoring of the reaction progress.

Reaction of photochemically generated acetylene 15 with primary, secondary, benzyl, and aryl azides produces corresponding triazoles 16a-c in quantitative yields. No other products were detected by GC/MS or TLC.

Example 2

The rate measurements of the cycloaddition reaction of acetylene 15 with azides was conducted by UV spectroscopy following the decay of the 317 nm band of 15 (as shown in FIG. 6) in the photolysate at various concentrations of azides from about 0.5 mM to about 20 mM). The reaction followed a first order equation, and the pseudo-first order rate constants were obtained by the by least-squares fitting of the data to a single exponential equation. The dependence of the observed rates on the concentration of azides was linear. The least-squares fitting of the data to a linear equation produced bimolecular rate constants summarized in Table 1.

TABLE 1

Bimolecular rate constants for the reaction of acetylene 15 with azides in methanol.

| Azide | Rate ($M^{-1} s^{-1}$) |
|---|---|
| n-Butyl azide | $5.86 \times 10^{-2}$ |
| 1-Phenyl-2-azidopropane | $3.43 \times 10^{-2}$ |
| Phenyl azide | $1.63 \times 10^{-2}$ |
| Benzyl azide | $7.63 \times 10^{-2}$ |

The rate constants of the cycloaddition reaction of acetylene 15 with azides was found to be similar to the recently reported rate of the reaction of difluoro-(Baskin et al., (2007) *Proc. Natl. Acad. Sci. U.S.A.* 104: 16793-16797) and dibenzo-substituted (Boons et al., (2008) *Angew. Chem., Int. Ed.* 47: 2253-2255) cyclooctynes with benzyl azide (2-[(6,6-difluoro-4-cyclooctyn-1-yl)oxy]-acetic acid: 0.076 $M^{-1}s^{-1}$; and 11,12-didehydro-5,6-dihydro-dibenzo[a,e]cycloocten-5-ol: 0.0568 $M^{-1}s^{-1}$.

Example 3

Figure 12:
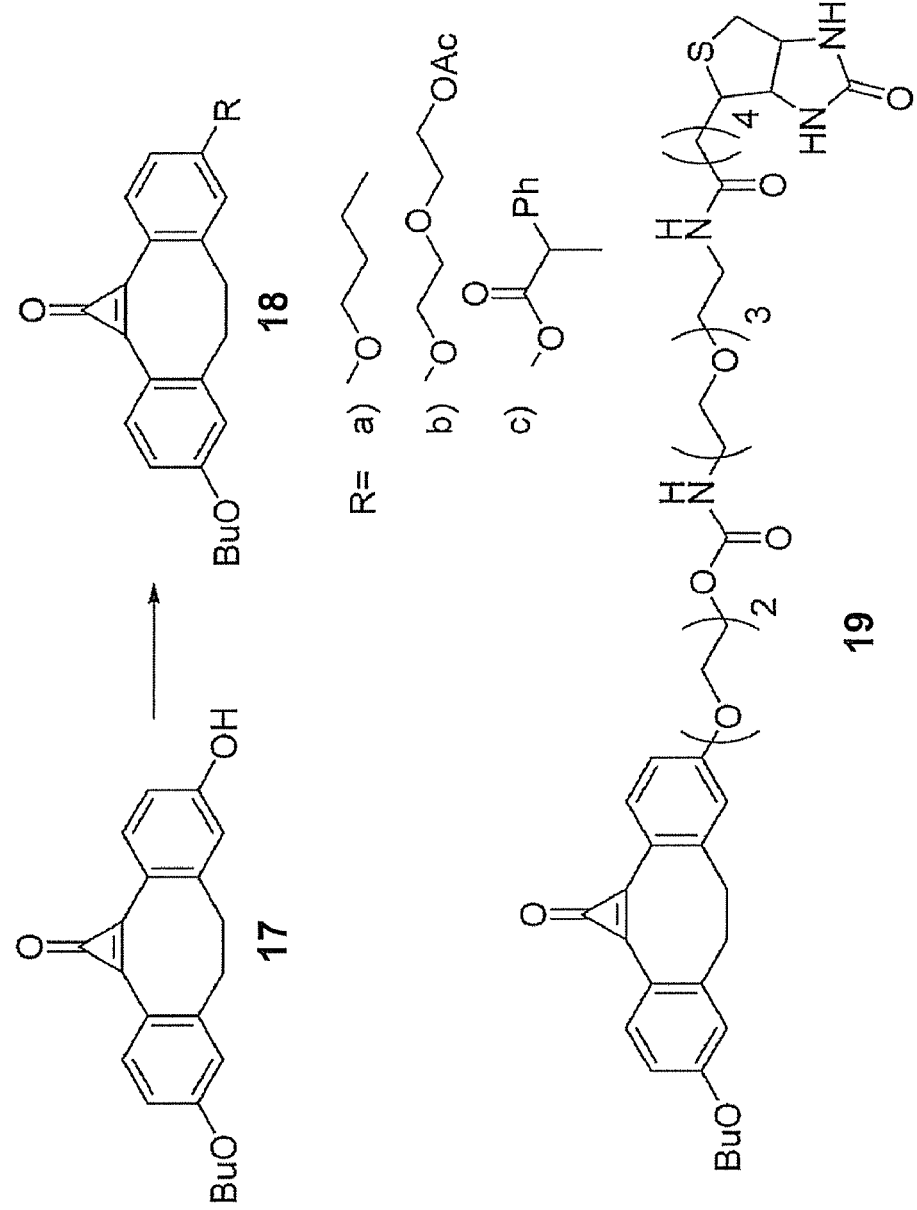
FIG. 12 illustrates a generalized scheme for cyclopropenone synthesis, where substituents may be attached to the cyclopropenone precursor by replacement of a hydroxyl group with a linker. The reaction of 17 with butanol or diethylene glycol acetate in the presence of $PPh_3$ and DEAD at 0° C. produces 18a and 18b. The reaction of 17 with a carboxylic acid in the presence of DCC and catalytic amount of DMAP provided ester 18c. Diethylene glycol-derivatized cyclopropenone 18b can be further linked to biotin, producing the biotin-cyclopropenone conjugate 19.

Substituents may be attached to the cyclopropenone precursor by replacement of one of the butoxy groups with an appropriate linker. To demonstrate this strategy cyclopropenone 17 was prepared (as shown in FIG. 12). The hydroxy group of the latter may be readily converted into an ether or an ester. Thus, the reaction of 17 with butanol or diethylene glycol acetate in the presence of PPh₃ and DEAD at 0° C. produced 18a and 18b in a good yield (see FIG. 12).

The reaction of 17 with a carboxylic acid in the presence of DCC and catalytic amount of DMAP provided ester 18c in 68% yield. Diethylene glycol-derivatized cyclopropenone 18b was further linked to biotin, producing the biotin-cyclopropenone conjugate 19 as shown in FIG. 12.

Diphenyl cyclopropenones, such as 14, 17, 18a-c, and 19, had long shelf lives, and could withstand elevated temperatures. Thus, the parent diphenylcyclopropenone was quantitatively recovered after stirring for 5 hours in DMSO at 130° C. (Poloukhtine & Popik (2003) *J. Org. Chem.* 68: 7833-7840). The cyclopropenones are also stable in solution in the absence of light. For example, cyclopropenone 14 showed no decomposition after incubation for 3 days at 40° C. in aqueous and methanol solutions.

Significantly, the cyclopropenones 14, 17, 18a-c, and 19 do not react with azides at room temperature.

Example 4

Figure 13:
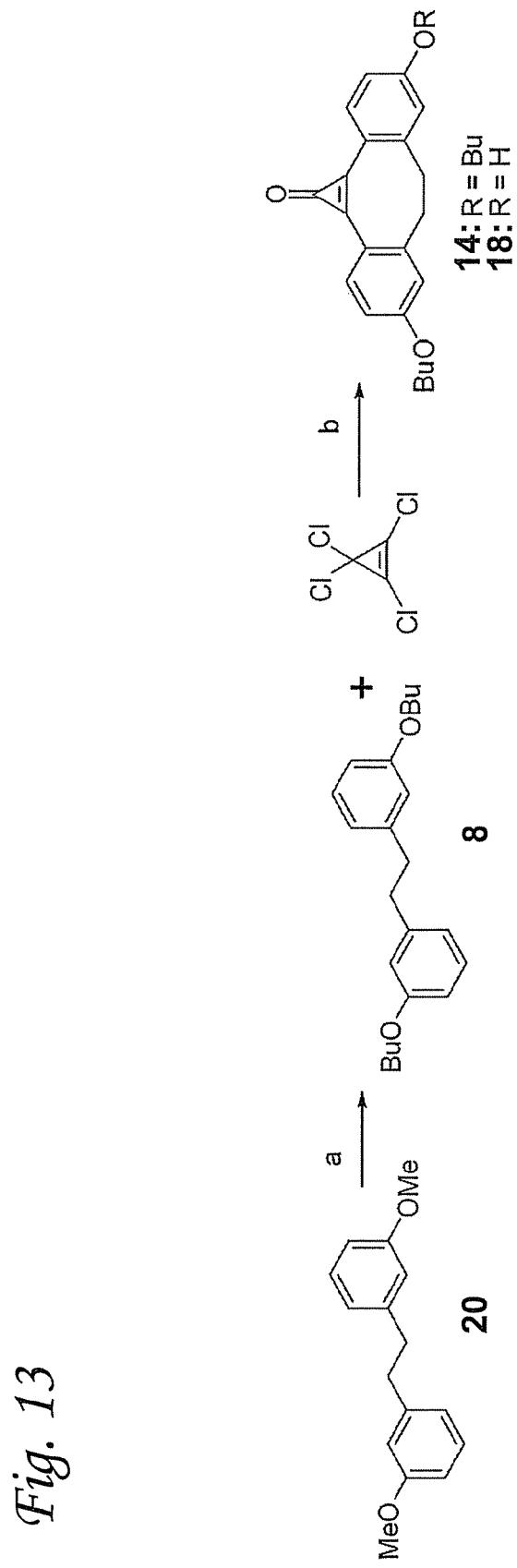
FIG. 13 illustrates a generalized scheme for the preparation of cyclopropenones 14 and 18. Reagents and conditions for the reactions were a) $BBr_3$, $CH_2Cl_2$; then BuBr, $K_2CO_3$, DMF; 72% over 2 steps; and c) $AlCl_3$, $CH_2Cl_2$, 35%.

Synthesis of vyclopropenone 14 and 18. A central step in the preparation of the cyclopropenones 14 and 18 is a double Friedel-Crafts reaction of 3,3'-dibutoxybibenzyl 8 with tetrachlorocyclopenone in the presence of anhydrous aluminum trichloride under medium dilution conditions (about 0.05 M in methylene chloride, as shown in FIG. 13).

The mono-hydroxy substituted cyclopropenone 18 was the major product of this reaction. Formation of bis-butoxy derivative 14 depended on the reaction conditions. Thus, after overnight incubation of the reaction mixture at room temperature, only 18 was isolated. However, incubation for only 5 hours resulted in formation of both 14 and 18 in 1:2 ratio.

Example 5

General Procedures

All NMR spectra were recorded in $CDCl_3$ and referenced to TMS unless otherwise noted. Melting points are uncorrected. Purification of products by column chromatography was performed using 40-63 micrometer silica gel. Tetrahydrofuran was distilled from sodium/benzophenone ketyl; ether and hexanes were distilled from sodium. Other reagents were obtained from Aldrich or VWR and used as received unless otherwise noted.

Materials 11,12-didehydro-5,6-dihydro-dibenzo[a,e]cycloocten-5-ol (4a) and 11,12-didehydro-5,6-dihydrodibenzo[a,e]cycloocten-5-yl ester of 19-[(3aS,4S,6aR)-hexahydro-2-oxo-1H-thieno[3,4-d]imidazol-4-yl]-15-oxo-5,8,11-trioxa-2,14-diazanonadecanoic acid (4b) were prepared as reported previously (Ning et al., *Angew. Chem. Int. Ed,* 2008, 47:2253-2255).

1,2-Bis(3-butoxyphenyl)ethane (8). $BBr_3$ (11.3 g, 45 mmol) was added to a solution of 1,2-bis(3-methoxyphenyl)ethane (Brunner et al., *Inorg. Chim. Acta* 2003, 350:39-48; 11.56 g; 47.8 mmol) in $CH_2Cl_2$ at −78° C. The reaction mixture was slowly warmed to room temperature, and stirred overnight. The reaction mixture was quenched with water, diluted with $CH_2Cl_2$, and the reaction mixture extracted with 2 M solution of NaOH (3×100 mL). The aqueous layer was slowly acidified at 0° C. with concentrated HCl to approximately pH=1, the grey precipitate was filtered, washed with water, dried in the air at room temperature, and then under vacuum at 85° C. over 5 hours to provide 10.3 g of crude 1,2-bis(3-hydroxyphenylethane as grey solid.

A suspension of crude 1,2-bis(3-hydroxyphenyl)ethane (10.3 g), BuBr (6.50 g, 143.4 mmol), and $K_2CO_3$ (20.08 g, 143.4 mmol) in DMF (70 mL) was stirred overnight at 75° C., cooled to room temperature, diluted with hexanes (approximately 150 mL) and water (approximately 250 mL). The organic layer was separated, washed with water, brine, dried over anhydrous $MgSO_4$, and concentrated. The residue was separated by chromatography (Hex:EtOAc 40:1) to provide 11.22 g, (72%, 34.42 mmol) of 1,2-bis(3-butoxyphenyl) ethane as slightly yellow oil that slowly crystallizes on standing. $^1$H NMR: 7.18 (dt, J=8.8, 1.2 Hz, 2H), 6.77 (d, J=8.0 Hz, 2H), 6.75-6.70 (m, 4H), 3.93 (t, J=6.4 Hz, 4H), 2.88 (s, 4H), 1.75 (5, J=6.4 Hz, 4H), 1.48 (six, J=7.2 Hz, 4H), 0.98 (t, J=6.8 Hz, 6H), 1.60-1.55 (m, 4H), 0.87 (s, 9H), 0.03 (s, 6H); $^{13}$C NMR: 159.4, 143.6, 129.5, 120.9, 115.0, 112.1, 67.8, 38.1, 31.6, 19.5, 14.1; MS calc for $C_{22}H_{30}O_2$ (M$^+$) 326.2246, EI-HRMS found 326.2280.

4-Butoxy-9-hydroxy-6,7-dihydro-1H-dibenzo[a,e]cyclopropa-[c][8]annulen-1-one (5a), and 4,9-dibutoxy-6,7-dihydro-1H-dibenzo[a,e]cyclopropa[c][8]annulen-1-one (5c).

Tetrachloro-cyclopropene was added to a suspension of $AlCl_3$ (2.45 g, 13.76 mmol) in $CH_2Cl_2$ (200 mL), the reaction mixture was stirred for 10 minutes at room temperature, and then cooled to −78° C. A solution of 8 (4.48 g, 13.76 mmol) in $CH_2Cl_2$ (approximately 10 mL) was added dropwise, and the reaction mixture was stirred for approximately 2 hours at −78° C., slowly warmed to room temperature, and stirred for an extra hour at room temperature. The reaction was quenched by 5% aqueous HCl solution, the organic layer was separated, washed with water, dried over anhydrous $MgSO_4$, and concentrated. The residue was separated by chromatography ($CH_2Cl_2$:MeOH 20:1) to provide 0.997 g (3.12 mmol, 23%) of 5a as yellow powder and 0.628 g (1.67 mmol, 12%) of 5c as white powder.

5a. $^1$H NMR (DMSO): 10.41 (s, 1H), 7.73 (d, J=8.4 Hz, 1H), 7.66 (d, J=8.4 Hz, 1H), 7.05 (d, J=2.4 Hz, 1H), 6.97 (dd, J=8.8, 2.4 Hz, 1H), 6.86 (d, J=2.4 Hz, 1H), 6.80 (dd, J=8.4, 2.4 Hz, 1H), 4.05 (t, J=6.4 Hz, 2H), 3.42-3.35 (m, 1H) 2.45-2.35 (m, 3H), 1.69 (p, J=7.2 Hz, 2H), 1.41 (six, J=7.6 Hz, 2H), 0.91 (t, J=7.2 Hz, 3H); $^{13}$C NMR: 158.9, 155.42, 155.19, 155.07, 127.1, 126.9, 117.5, 116.96, 116.72, 116.1, 113.3, 112.1, 110.79, 110.34, 68.1, 36.8, 36.7, 31.5, 19.5, 14.1. MS calc for $C_{21}H_{21}O_3$ (MH$^+$) 321.1491, APCI-HRMS found 321.1482.

5c. $^1$H NMR: 7.73 (d, J=9.6 Hz, 2H), 6.69 (m, 4H), 4.04 (t, J=6.0 Hz, 4H), 3.33 (d, J=10.4 Hz, 2H), 2.63 (d, J=10.4 Hz, 2H), 1.80 (p, J=6.0 Hz, 4H), 1.52 (s, J=7.6 Hz, 4H), 1.00 (t, J=7.6 Hz, 6H); $^{13}$C NMR: 162.3, 154.0, 148.0, 142.3, 136.0, 116.5, 112.5, 68.2, 37.4, 31.4, 19.42, 14.03.

2-[2-(9-Butoxy-6,7-dihydro-1H-dibenzo[a,e]cyclopropa[c][8]annulen-1-one) ethoxy]ethyl acetate (9). A solution of DEAD (0.635 g, 3.75 mmol) in THF (approximately 5 mL) was added to a solution of 5a (0.75 g, 2.34 mmol), $PPh_3$ (0.983 g, 3.75 mmol), and 2-(2-hydroxyethoxy)ethyl acetate (0.44 g, 3.0 mmol) in THF (100 mL) at room temperature, and the reaction mixture was stirred for 30 minutes at room temperature. Solids were separated by filtration, solvents were removed in vacuum, and the residue separated by chromatography (Hex:ExOAc 2:1→Hex:ExOAc:$CH_2Cl_2$ 4:3:1 Hex:ExOAc:$CH_2Cl_2$ 5:5:4+5% of MeOH) to produce 0.971 g (2.16 mmol, 92%) of 9 as slightly yellow oil that crystallizes on standing. $^1$H NMR: 7.93 (d, J=8.4 Hz, 2H), 6.94-6.86 (m, 4H), 4.27 (t, J=4.4 Hz, 2H), 4.22 (t, J=4.4 Hz, 2H), 4.04 (t, J=6.0 Hz, 2H), 3.90 (t, J=4.4 Hz, 2H), 3.72 (t, J=4.4 Hz, 2H), 3.33 (d, J=10.4 Hz, 2H), 2.62 (d, J=11.2 Hz, 2H), 2.09 (s, 3H), 1.80 (p, J=7.2 Hz, 2H), 1.52 (six, J=7.6 Hz, 2H), 1.00 (t, J=7.2 Hz, 3H); $^{13}$C NMR: 171.3, 162.1, 161.5, 153.5, 147.81, 147.78, 142.5, 135.8, 135.7, 116.7, 116.4, 116.36, 116.13, 112.32, 112.30, 69.43, 69.39, 68.0, 67.6, 63.5, 37.2, 31.1, 21.0, 19.2, 13.8.

2-{2-[(9-Butoxy-5',5'-dimethyl-6,7-dihydrospiro-[dibenzo[a,e]cyclopropa[c][8]annulene-1,2'-[1,3]dioxan]-4-yl)oxy]ethoxy}ethyl acetate (10). $BF_4O(C_2H_5)$ (0.45 g, 2.38 mmol, 1.1 eq) was added to a solution of cyclopropenone 9 (0.971 g, 2.16 mmol) in $CH_2Cl_2$ (5 mL) at room temperature, and the resulting solution was stirred for 20 minutes at room temperature. A solution of neopentyl glycol (0.270 g, 2.59 mmol, 1.2 eq) and $Et_3N$ (0.330 g, 3.24 mmol, 1.5 eq) in $CH_2Cl_2$ (approximately 1.5 mL) was added at room temperature, the reaction mixture was stirred for 20 minutes at room temperature, and solvents were removed under reduced pressure. The residue was separated by chromatography (Hex:ExOAc 5:1+1.5% of $Et_3N$→Hex:ExOAc 1:1+1.5% of $Et_3N$→Hex:ExOAc:$CH_2Cl_2$ 5:5:4+5% of MeOH and 1.5% of $Et_3N$) to provide 0.593 g (1.11 mmol, 96% calculated on consumed substrate) of cyclopropenone acetal 10 as slightly yellow oil, and 0.431 g (0.96 mmol) of unreacted cyclopropenone 9. $^1$H NMR: 7.65 (dd, J=8.4, 2.4 Hz, 2H), 6.92-6.82 (m, 4H), 4.26 (t, J=4.4 Hz, 2H), 4.18 (t, J=4.4 Hz, 2H), 4.00 (t, J=6.4 Hz, 2H), 3.9a (m, 4H), 3.88 (t, J=4.4 Hz, 2H), 3.78 (t, J=4.4 Hz, 2H), 3.24 (d, J=10.4 Hz, 2H), 2.41 (d, J=11.2 Hz, 2H), 2.08 (s, 3H), 1.79 (p, J=7.2 Hz, 2H), 1.51 (six, J=7.6 Hz, 2H), 1.21 (s, 3H), 1.19 (s, 3H), 0.99 (t, J=7.2 Hz, 3H); $^{13}$C NMR: 171.1, 159.6, 159.0, 147.1, 131.5, 131.4, 124.2, 123.4, 119.5, 118.9, 116.05, 115.94, 111.97, 111.92, 83.9, 79.2, 69.6, 69.4, 63.5, 36.9, 31.3, 30.6, 22.62, 22.59, 21.0, 19.2, 13.9.

2-{2-[(9-Butoxy-5',5'-dimethyl-6,7-dihydrospiro-[dibenzo[a,e]cyclopropa[c][8]annulene-1,2'-[1,3]dioxan]-4-yl)oxy]ethoxy}ethanol (11). A solution of NaOH (1.2 mL, 1.2 mmol, 1 M aqueous solution) was added to solution of acetate 10 (0.593 g, 1.11 mmol) in MeOH:THF (10:3 mL) at room temperature, and the reaction mixture was stirred for 30 minutes at room temperature. The reaction mixture was partially concentrated under reduced pressure, diluted with EtOAc (approximately 25 mL) and water (approximately 10 mL), the organic layer was separated, washed with brine, and dried over anhydrous MgSO$_4$. Solvents were evaporated under reduced pressure, and the residue was separated by chromatography (Hex:ExOAc:CH$_2$Cl$_2$ 3:2:1+1.5% of Et$_3$N) to provide 0.493 g (0.89 mmol, 81%) of an alcohol 11 as slightly yellow oil that crystallizes on standing. $^1$H NMR: 7.65 (dd, J=8.4, 2.4 Hz, 2H), 6.92-6.82 (m, 4H), 4.18 (t, J=4.4 Hz, 2H), 4.04 (t, J=6.4 Hz, 2H), 3.92 (m, 4H), 3.88 (t, J=4.4 Hz, 2H), 3.77 (t, J=4.4 Hz, 2H), 3.68 (t, J=4.4 Hz, 2H), 3.24 (d, J=10.8 Hz, 2H), 2.41 (d, J=10.8 Hz, 2H), 1.76 (p, J=7.2 Hz, 2H), 1.50 (six, J=7.6 Hz, 2H), 1.21 (s, 3H), 1.19 (s, 3H), 0.99 (t, J=7.2 Hz, 3H); $^{13}$C NMR: 159.8, 159.2, 147.4, 131.84, 131.75, 131.67, 131.57, 124.4, 123.6, 119.8, 119.1, 116.3, 116.2, 112.2, 84.1, 79.4, 72.8, 69.8, 68.0, 76.7, 62.0, 37.1, 31.5, 30.8, 22.9, 19.4, 14.2.

2-{2-[(9-Butoxy-5',5'-dimethyl-6,7-dihydrospiro-[dibenzo[a,e]cyclopropa[c][8]annulene-1,2'-[1,3]dioxan]-4-yl)oxy]ethoxy}ethyl 4-nitrophenyl carbonate (12). A solution of alcohol 11 (0.439 g, 0.89 mmol) and pyridine (0.25 g, 3.21 mmol) in CH$_2$Cl$_2$ (approximately 5 mL) was added to a solution of 4-nitrophenyl chloroformate (0.30 g, 1.49 mmol) in CH$_2$Cl$_2$ (25 mL) at room temperature, and the reaction mixture was stirred for 20 minutes at room temperature. Solvent was evaporated under reduced pressure, and the residue was separated by chromatography (Hex:ExOAc 4:1+1.5% of Et$_3$N) to provide 0.317 g (0.48 mmol 80%) of 12 as and 0.113 g (0.23 mmol) of starting 11. $^1$H NMR: 8.25 (d, J=8.8 Hz, 2H) 7.65 (dd, J=8.4, 2.0 Hz, 2H), 7.35, (d, J=9.2 Hz, 2H), 6.92-6.82 (m, 4H), 4.43 (t, J=4.4 Hz, 2H), 4.19 (t, J=6.4 Hz, 2H), 3.98 (t, J=4.4 Hz, 2 H), 3.92 (m, 7H), 3.22 (d, J=10.8 Hz, 2H), 2.43 (d, J=10.8 Hz, 2H), 1.75 (p, J=7.2 Hz, 2H), 1.51 (six, J=7.6 Hz, 2H), 1.21 (s, 3H), 1.19 (s, 3H), 0.98 (t, J=7.2 Hz, 3H); $^{13}$C NMR: 159.9, 159.2, 155.7, 152.7, 150.0 147.4, 145.6, 131.77, 131.63, 125.5, 124.6, 123.4, 122.0, 119.8, 119.1, 116.25, 116.19, 112.2, 112, 15, 84.1, 79.4, 70.0, 69.1, 68.4, 70.0, 67.8, 37.1, 31.5, 30.8, 22.87, 22.79, 19.5, 14.1.

2-{2-[(9-Butoxy-1-oxo-6,7-dihydro-1H-dibenzo[a,e]cyclopropa-[c][8]annulen-4-yl)oxy]ethoxy}ethyl {2-[2-(2-{[5-(2-oxohexahydro-1H-thieno[3,4-d]imidazol-4-yl)pentanoyl]amino}ethoxy)ethoxy]ethyl}carbamate (5b). A solution of cyclopropenone acetal 12 (0.21 g, 0.312 mmol) in DMF (approximately 2 mL) was added to a solution of Et$_3$N (0.18 g, 1.75 mmol) and N-Boc-N'-biotinyl-3,6-dioxaoctane-1,8-diamine (Ning et al., *Angew. Chem. Int. Ed.* 2008, 47:2253-2255) (0.13 g, 0.35 mmol) in DMF (35 mL) at room temperature. The reaction mixture was stirred overnight at room temperature, most solvent was evaporated under reduced pressure, and the residue was passed thought a short silica gel column (CH$_2$Cl$_2$:MeOH 25:1+1.5% of Et$_3$N) to provide 0.275 g of crude product 13 that used in next step without any further purification.

A suspension of crude cyclopropenone acetal 13 (0.199 g) and Amberlyst 15 (0.10 g) in Me$_2$CO (10 mL) was stirred for 60 minutes at room temperature. Solids were removed by filtration, solvent was evaporated under reduced pressure, and the residue was separated by chromatography (CH$_2$Cl$_2$: MeOH 10:1) to provide 17 mg of cyclopropenone 5b as an amorphous solid. $^1$H NMR: 7.65 (dd, J=8.4, 3.0 Hz, 2H), 6.93-6.87 (m, 4H), 6.66 (s, b, 1H), 6.25, (s, b, 1H) 5.61 (m, b, 1H) 5.39 (s, b, 1H) 4.48 (m, b, 1H), 4.30-4.24 (m, 4H), 4.21 (t, J=5.0 Hz, 2H), 4.05 (t, J=7.5 Hz, 2H), 3.88 (t, J=5.5 Hz, 2H), 3.78 (m, 2H), 3.60 (s, 4H), 3.44 (q, J=6.5 Hz, 2H), 3.40-3.30 (m, 4H), 3.18-3.1 (m, 3H), 2.27 (dd, J=16.0, 6.0 Hz, 1H), 2.73 (d, J=16.0 Hz, 1H), 2.62 (d, J=14.0 Hz, 2H), 2.20 (t, J=9.0 Hz, 2H), 2.19-2.02 (m, 4H), 1.81 (p, J=8.5 Hz, 2H), 1.74-1.60 (m, 4H), 1.51 (six, J=9.0 Hz, 2H), 1.46-1.4 (m, 2H), 1.36 (t, J=9 Hz, 2H), 1.00 (t, J=9.5 Hz, 3H); $^{13}$C NMR: 173.4, 163.8, 162.2, 161.5, 156.5, 153.8, 147.86, 147.83, 142.5, 141.9, 135.85, 135.76, 116.71, 116.4, 116.28, 116.14, 112.39, 112.34, 70.13, 70.07, 69.99, 69.88, 69.4, 68.0, 67.7, 63.9, 62.8, 60.2, 55.5, 45.8, 40.8, 40.5, 39.1, 37.20, 37.15, 35.8, 31.1, 28.13, 28.07, 25.5, 19.2, 13.8, 8.6; MS calc for C$_{41}$H$_{56}$N$_4$O$_9$S (M$^+$–CO+Na) 803.3666, ESI-HMS found 808.3677.

Independent Preparation of Biotinylated Acetylene 6b

2-{2-[(9-Butoxy-5,6-didehydro-11,12-dihydrodibenzo[a,e][8]annulen-2-yl)oxy]ethoxy}ethanol (15). A solution of cyclopropenone 9 (0.54 g, 1.35 mmol) in MeOH:THF (1:1 v:v, 60 mL) was irradiated with 350 nm lamps for ca. 20 minutes. Solution was concentrated to 10 mL under reduced pressure, and 1 M aqueous NaOH solution (1.68 mL, 1.68 mmol) was added to the reaction mixture and stirred at room temperature for approximately 30 minutes. Ethyl acetate was added to the reaction mixture, the organic layer was separated, washed with water, brine, dried over anhydrous MgSO$_4$ and solvent removed in vacuum. The residue was separated by chromatography (EtOAc:Hex 1:1.5) to provide 0.375 g (0.99 mmol, 73%) of alcohol 15 as an amorphous white solid. $^1$H NMR: 7.20 (dd, J=8.4, 0.8 Hz, 2H), 6.87 (dd, J=11.2 Hz, 2.0, 2H), 6.75 (td, J=8.0, 2.4 Hz, 2H), 4.15 (t, J=4.4 Hz, 2 H), 3.97 (t, J=6.0 Hz, 2H), 3.87 (t, J=4.4 Hz, 2H), 3.76 (s, b, 2H), 3.68 (t, J=4.4 Hz, 2H), 3.17 (d, J=11.2 Hz, 2H), 2.43 (d, J=10.4 Hz, 2H), 1.77 (p, J=7.2 Hz, 2H), 1.50 (six, J=7.2 Hz, 4H), 0.98 (t, J=7.2 Hz, 6H); $^{13}$C NMR: 158.9, 158.3, 155.1, 126.99, 126.84, 117.05, 116.93, 116.10, 112.08, 112.05, 110.91, 110.39, 72.8, 69.8, 68.0, 67.7, 62.0, 36.94, 36.77, 31.5, 19.5, 14.1, 14.01. MS calc for C$_{24}$H$_{28}$O$_4$ (M$^+$) 380.1988, EI-HRMS found 380.1982.

2-{2-[(9-Butoxy-5,6-didehydro-11,12-dihydrodibenzo[a, e][8]annulen-2-yl)oxy]ethoxy}ethyl 3-nitrophenyl carbonate (16). A solution of pyridine (0.20 g, 2.60 mmol) in CH$_2$Cl$_2$ (approximately 1 mL) was added to a solution of alcohol 15 (0.24 g, 0.63 mmol) and 4-nitrophenyl chloroformate (0.20 g, 1.00 mmol) in CH$_2$Cl$_2$ (5 mL) at room temperature, and the reaction mixture was stirred for 3 hours. Solvent was evaporated under reduced pressure, and the residue was separated by chromatography (Hex:ExOAc 4:1) to provide 0.34 g (0.63 mmol 99%) of 16 as slightly yellow oil. $^1$H NMR: 8.25 (d, J=8.8 Hz, 2H), 7.36 (d, J=9.2 Hz, 2H), 7.19 (d, J=8.8 Hz, 2H), 6.89 (dd, J=14.0, 2.4 Hz, 2H), 6.79-6.75 (m, 2H), 4.47 (t, J=4.4 Hz, 2H), 4.18 (t, J=4.4 Hz, 2H), 3.97 (t, J=6.6 Hz, 2H), 3.92-3.88 (m, 4H), 3.17 (d, J=10.8 Hz, 2H), 2.42 (d, J=10.8 Hz, 2H), 1.77 (p, J=7.2 Hz, 2H), 1.49 (six, J=7.2 Hz, 4H), 0.98 (t, J=7.2 Hz, 6H); $^{13}$C NMR: 158.9, 158.3, 155.7, 155.13, 155.08, 152.7, 145.6, 127.0, 126.9, 112.1, 121.9, 117.0, 116.97, 116.94, 112.15, 112.11, 112.00, 111.0, 110.3, 70.1, 69.1, 68.5, 68.0, 67.8, 36.9, 36.7, 31.5, 19.5, 14.2, 14.0.

2-{2-[(9-Butoxy-5,6-didehydro-11,12-dihydrodibenzo[a, e][8]annulen-2-yl)oxy]ethoxy}ethyl {2-[2-(2-{[5-(2-oxo-hexahydro-1H-thieno[3,4-d]imidazol-4-yl)pentanoyl] amino}ethoxy)ethoxy]ethyl}carbamate (6b). A solution of carbonate 16 (0.15 g, 0.28 mmol) in DMF (approximately 2 mL) was added to a solution of $Et_3N$ (0.5 g, 4.95 mmol) and N-Boc-N'-biotinyl-3,6-dioxaoctane-1,8-diamine (Ning et al., *Angew. Chem. Int. Ed.* 2008, 47:2253-2255) (0.01 g, 0.28 mmol) in DMF (10 mL) at room temperature. The reaction mixture was stirred overnight at room temperature, most solvent was evaporated under reduced pressure, and the residue was separated by chromatography on ($CH_2Cl_2$:MeOH 30:1) to provide 0.164 g (0.21 mmol, 75%) of 16. $^1H$ NMR δ 7.19 (d, J=8.4 Hz, 2H), 6.88 (dd, J=9.5, 2.5 Hz, 2H), 6.76 (td, J=8.2, 2.5, 2H), 6.74-6.65 (m, 1H), 6.54 (s, b, 1H), 5.74 (s, b, 1H), 5.60 (s, b 1H), 4.49-4.43 (m, 1H), 4.29-4.22 (m, 3H), 4.16-4.10 (m, 2H), 3.97 (t, J=6.5, 2H), 3.87-3.81 (m, 2H), 3.76 (m, 2H), 3.59-3.48 (m, 10H), 3.42 (m, 2H), 3.37-3.12 (m, 2H), 3.21-3.09 (m, 4H), 2.86 (dd, J=12.6, 4.7 Hz, 1H), 2.72 (d, J=12.7, 1H), 2.42 (d, J=10.9, 2H), 2.21 (t, J=7.4, 4H), 1.81-1.56 (m, 6H), 1.48 (six, J=7.4 Hz, 2H), 1.44-1.36 (m, 2H), 1.32 (t, J=7.4 Hz, 1H), 0.98 (t, J=7.4, 3H); $^{13}C$ NMR δ 173.4, 164.1, 158.7, 158.1, 156.5, 154.8, 126.66, 126.63, 116.80, 116.72, 116.59, 115.8, 111.91, 111.83, 110.67, 110.14, 70.09, 70.04, 69.95, 69.90, 69.80, 69.54, 67.78, 67.52, 63.88, 61.80, 60.2, 55.6, 45.6, 40.8, 40.5, 39.1, 36.63, 36.61, 35.9, 31.3, 28.22, 28.08, 25.6, 19.2, 13.8, 8.5.

General Procedure for Preparative Photolyses of Cyclopropenones 5

3,9-Dibutoxy-5,6-didehydro-11,12-dihydrodibenzo[a,e] [8]annulen-2-yl (3c). A solution of cyclopropenone 5c (0.20 g, 0.532 mmol) in MeOH (20 mL, 2.72×$10^{-2}$M) was irradiated (4×350 nm) for 20 minutes at room temperature. The solvent was evaporated under vacuum, and the residue was separated by column chromatography (Hex:EtOAc 1:20) to provide 0.160 g (0.459 mmol, 86%) of 6b as slightly yellow oil. NMR: 7.19 (d, J=8.4 Hz, 2H), 6.87 (d, J=2.4 Hz, 2H), 6.75 (dd, J=8.4, 2.4 Hz, 2H), 3.97 (t, J=6.4 Hz, 4H), 3.18 (d, J=11.2 Hz, 2H), 2.44 (d, J=11.2 Hz, 2H), 1.77 (p, J=7.2 Hz, 4H), 1.52 (six, J=7.2 Hz, 4H), 0.98 (t, J=7.2 Hz, 6H); $^{13}C$ NMR: 158.9, 155.1, 126.9, 116.9, 116.2, 112.0, 110.6, 68.0, 36.9, 31.5, 19.5, 14.1.

General Procedure for the Preparation of Triazoles 7

A solution of 6c (0.5 mmol) and appropriate organic azide (0.75 mmol) in MeOH was stirred overnight at room temperature. The solvent was evaporated under reduced pressure, and the excess of aizde was removed by chromatography on silica gel.

1-Phenyl-6,11-dibutoxy-8,9-dihydro-1H-dibenzo[3,4:7, 8]cycloocta[1,2-d][1,2,3]triazole (7a, R=Ph). NMR: 7.53 (d, J=8.8 Hz, 1H), 7.39 (s, 5H), 6.85 (d, J=2.4 Hz, 1H), 6.79 (dd, J=8.4, 2.4 Hz, 1H), 6.74 (d, J=2.4 Hz, 1H), 6.62 (d, J=8.8 Hz, 1H), 6.51 (dd, J=8.4, 2.8 Hz, 1H), 3.94 (t, J=6.4 Hz, 2H), 3.89 (t, J=6.4 Hz, 2H), 3.50-3.30 (m, 2H), 3.17-2.92 (m, 2H), 1.78-1.68 (m, 4H), 1.46 (sep, J=7.2 Hz, 4H), 0.96 (t, J=7.2 Hz, 3H), 0.95 (t, J=7.2 Hz, 3H); $^{13}C$ NMR: 159.9, 159.2, 147.0, 142.5, 139.7, 137.0, 133.6, 133.0, 131.8, 129.5, 128.8, 124.8, 122.5, 118.8, 116.5115.8, 112.8, 112.6, 67.81, 67.77, 36.2, 34.2, 31.5, 19.47, 19.45, 14.10, 14.07.

6,11-Dibutoxy-1-butyl-8,9-dihydro-1H-dibenzo[3,4:7,8] cycloocta[1,2-d][1,2,3]triazole (7a, R=n-Bu) NMR: 7.43 (d, J=8.4 Hz, 1H), 7.06 (d, J=8.4 Hz, 1H), 6.87 (d, J=2.4 Hz, 1H), 6.78 (dd, J=8.4, 2.4 Hz, 1H), 6.75 (dd, J=8.4, 2.4 Hz, 1H) 6.67 (d, J=2.4 Hz, 1H), 4.42-4.24 (m, 2H), 3.96 (t, J=6.4 Hz, 2H), 3.93 (t, J=6.8 Hz, 2H), 3.40-3.32 (m, 1H), 3.14-2.98 (m, 2H), 2.88-2.78 (m, 1H), 1.86-1.68 (m, 6H), 1.54-1.41 (m, 4H), 1.34-1.18 (m, 2H), 0.98 (t, J=7.6 Hz, 3H), 0.95 (t, J=7.2 Hz, 3H), 0.85 (t, J=7.2 Hz, 3H); $^{13}C$ NMR: 160.1, 158.9, 146.6, 143.3, 139.2, 133.6, 133.2, 130.2, 122.8, 118.9, 116.6, 115.9, 112.9, 112.567.9, 67.7, 48.2, 36.9, 33.4, 32.3, 31.55, 31.50, 19.8, 19.5, 14.1, 13.7.

Kinetic Experiments

Rate measurements were performed using Carry-300 Bio UV-Vis spectrometer equipped with a thermostatable cell holder. The temperature was controlled with 0.1° C. accuracy. A solution of 6c in MeOH (ca. 6×$10^{-5}$ M) in 1 cm quarts cell was thermally equilibrated for at least 30 minutes at 25±0.1° C. A calculated amount of 0.25 M solutions of an azide required to achieve desired azide concentration (6×$10^{-1}$-1.5× $10^{-2}$M) was added at once. Reactions were monitored by following the decay of the characteristic absorbance of acetylene 6c at approximately 317 nm (FIG. 6). The reaction follows a first order equation well and the pseudo-first order rate constants were obtained by the by least-squares fitting of the data to a single exponential equation. The dependence of the observed rates on the concentration of azides was linear. The least-squares fitting of the data to a linear equation produced bimolecular rate constants summarized in Table 3.

TABLE 3

Bimolecular rate constants for the reaction of acetylene 6c with azides in methanol.

| Azide | Rate ($M^{-1} s^{-1}$) |
|---|---|
| n-Butyl azide | 5.86 × $10^{-2}$ |
| 1-Phenyl-2-azidopropane | 3.43 × $10^{-2}$ |
| Phenyl azide | 1.63 × $10^{-2}$ |
| Benzyl azide | 7.63 × $10^{-2}$ |

General Conditions for Biological Experiments

Synthetic compounds 4b, 5b, and 6b were reconstituted in DMF and stored at −80° C. Final concentrations of DMF never exceeded 0.56% to avoid toxic effects. For the in situ photo-activation of biotinilated cyclopropenone 5b minphotoreactor available under the trade designation Rayonet equipped with 350 nm florescent tubes was employed.

Cell Culture Conditions

Human Jurkat cells (Clone E6-1; ATCC) were cultured in RPMI 1640 medium (ATCC) with L-glutamine (2 mM), adjusted to contain sodium bicarbonate (1.5 g/L), glucose (4.5 g/L), HEPES (10 mM), and sodium pyruvate (1 mM) and supplemented with penicillin (100 u/ml)/streptomycin (100 micrograms/mL; Mediatech) and fetal bovine serum (FBS, 10%; Hyclone). Chinese hamster ovary (CHO) cells (Clone K1; ATCC) were cultured in Kaighn's modification of Ham's F-12 medium (F-12K) with L-glutamine (2 mM), adjusted to contain sodium bicarbonate (1.5 g $L^{-1}$) and supplemented with penicillin (100 u $mL^{-1}$)/streptomycin (100 micrograms $mL^{-1}$) and FBS (10%). Cells were maintained in a humid 5% $CO_2$ atmosphere at 37° C.

Cell Surface Azide Labeling

Jurkat cells were seeded at a density of 75,000 cells $mL^{-1}$ in a total volume of 40 mL culture medium in the presence of peracetylated N-azidoacetylmannosamine ($Ac_4$ManNaz; 25 micromolar final concentration) and grown for 3 days, leading to the metabolic incorporation of the corresponding N-azidoacetyl sialic acid (SiaNAz) into their cell surface glycoproteins. Control cells were grown in the presence of peracetylated N-acetylmannosamine ($Ac_4$ManNac; 25 micromolar final concentration) for 3 days. Similarly, CHO cells were grown for 3 days in the presence of $Ac_4$ManNaz (100 micromolar final concentration) or Ac₄ManNac (100 micromolar final concentration).

Click Chemistry and Detection by Fluorescence Intensity

Jurkat cells bearing azides and control cells were washed with labeling buffer (DPBS, pH 7.4 containing 1% FBS and 1% BSA), transferred to round bottom tubes (1×10⁶ cells/sample) and incubated with the biotinylated compounds 4b, 5b, or 6b (0-100 micromolar) in labeling buffer for 0-90 minutes at room temperature. To activate 5b in situ, immediately after adding the compound to the cells, the cell suspension was subjected to UV light (350 nm) for 1 minute. The cells were washed three times with cold labeling buffer and then incubated with avidin conjugated with fluorescein (0.5 microgram/ml; Molecular Probes) for 15 minutes at 4° C. Following three washes and cell lysis in passive lysis buffer (Promega), cell lysates were analysed for fluorescence intensity (485 ex/520 em) using a microplate reader (BMG Labtech). Data points were collected in triplicate and are representative of three separate experiments. Fluorescence of Jurkat cell lysates was expressed as fluorescence (arbitrary units; AU) per 800,000 cells.

Measurement of Cytotoxicity

Cell viability and cell morphology were assessed by exclusion of trypan blue followed microscopic evaluation immediately after photoactivation or after reincubation of the labeled cells in cell culture medium for 5 hours or overnight. Viability was measured by quantifying the cellular ability to reduce the water-soluble tetrazolium dye 3-4,5-dimethylthiazole-2,5-diphenyl tetrazolium bromide (MTT) to its insoluble formazan salt (e.g., Sgouras et al., *J. Mater. Sci.: Materials in Medicine* 1990, 1:61-68). Data points were collected in triplicate and expressed as normalized values for control cells (100%).

Western Blot Analysis

Jurkat cells were harvested by centrifugation (5 minutes at 1,400 rpm) and resuspended as 5×10⁶ cells/mL. The cell suspensions (250 microliters per sample) were incubated with biotin-conjugated alkynes 4b, 5b, and 6b (30 micromolar) or without compound as control for 1 hour. To activate 5b in situ, immediately after adding the compound to the cells, the cell suspension was subjected to UV light (350 nm) for 1 minute. The cells were washed (4×10 minutes) with cold DPBS, pH 7.4 containing FBS (1%) and lysed in passive lysis buffer. The cell lysates were clarified by centrifugation at 15,000 rpm for 15 minutes and the total protein content of the clear supernatants was assessed using the bicinchonic acid assay (BCA; Pierce Biotechnology). Cell lysate samples (20 micrograms protein) in SDS-PAGE sample buffer containing 2-mercaptoethanol were boiled for 5 minutes, resolved on a 4-20% Tris-HCl gel (Bio-Rad) and transferred to nitrocellulose membrane. Next the membrane was blocked in blocking buffer (non-fat dry milk (5%; Bio-Rad) in PBST (PBS containing 0.1% Tween-20 and 0.1% Triton X-100)) for 2 hours at room temperature. The blocked membrane was incubated for 1 hour at room temperature with an anti-biotin antibody conjugated to horseradish peroxidase (HRP) (1:100,000; Jackson ImmunoResearch Lab, Inc.) in blocking buffer and washed with PBST (4×10 minutes). Final detection of HRP activity was performed using ECL Plus chemiluminescent substrate available under the trade designation Amersham), exposure to film (Kodak) and development using a digital X-ray imaging machine (Kodak). The gel was stained by Coomassie to confirm total protein loading.

Detection of Cell Labeling by Fluorescence Microscopy.

CHO cells bearing azides and untreated control cells were transferred to glass coverslips and cultured for 36 hours in their original medium. Live CHO cells were treated with the biotinylated compound 5b (30 micromolar) in labeling buffer (DPBS, supplemented with FBS (1%)) for 1 hour at room temperature. To activate 5b in situ, immediately after adding the compound to the cells, the cells were subjected to UV light (350 nm) for 1 minute. Next, the cells were incubated with avidin conjugated with Alexa Fluor 488 (Molecular Probes) for 15 minutes at 4° C. Cells were washed 3 times with labeling buffer and fixed with formaldehyde (3.7% in PBS). The nucleus was labeled with the far red-fluorescent TO-PRO-3 dye (Molecular Probes). The cells were mounted with PermaFluor (Thermo Electron Corporation) before imaging. Initial analysis was performed on a Zeiss Axioplan2 fluorescent microscope. Confocal images were acquired using a 60× (NA1.42) oil objective. Stacks of optical sections were collected in the z dimensions. The step size, based on the calculated optimum for each objective, was between 0.25 and 0.5 micrometers. Subsequently, each stack was collapsed into a single image (z-projection). Analysis was performed offline using ImageJ 1.39f software (National Institutes of Health, USA) and Adobe Photoshop CS3 Extended Version 10.0 (Adobe Systems Incorporated), whereby all images were treated equally.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

What is claimed is:

1. A compound having the formula:

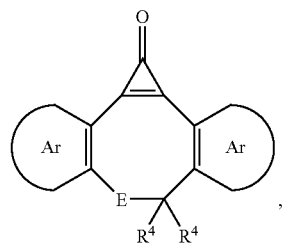

wherein each Ar is a phenyl group; E represents $C(R^4)_2$; and each $R^4$ is independently selected from the group consisting of hydrogen, halogen, hydroxy, alkoxy, nitrate, nitrite, sulfate, a C1-C10 organic group, and a linking group;

wherein at least one Ar is a phenyl group in which one or more carbon atoms of the phenyl group are substituted with a substituent selected from the group consisting of alkyl, aryl, heteroaryl, halogen, nitro, cyano, hydroxyl, alkoxyl, aryloxyl; thio, mercapto, alkylthio, arylthio, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, carboxyl, alkyloxycarbonyl, aryloxycarbonyl, aldehyde, arylcarbonyl, alkylcarbonyl, iminyl, aryliminyl, alkyliminyl, sulfo, alkylsulfonyl, arylsulfonyl, hydroximinyl, aryloximinyl, and alkoximinyl; and wherein two or more alkyl or heteroalkyl substituents of a phenyl group may optionally be combined to form fused aryl-alkyl or aryl-heteroalkyl ring systems.

2. A compound having the formula:

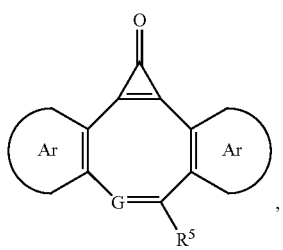

wherein each Ar is a phenyl group; G represents $CR^6$; and each $R^5$ and $R^6$ is independently selected from the group consisting of hydrogen, halogen, hydroxy, alkoxy, nitrate, nitrite, sulfate, a C1-C10 organic group, and a linking group.

3. A compound having the formula I:

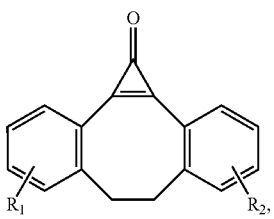

wherein:
R$^1$ is selected from the group consisting of: an alkoxy and a hydroxyl;
R$^2$ is selected from the group consisting of: an alkyl, a heteroalkyl, a cycloalkyl, a heterocycloalkyl, an aryl, an alkoxy, a carboxy, a hydroxyl, an ether, an ester, and a halogen; and
the cyclooctyne is a dibenzocyclooctyne.

4. The compound of claim 3 wherein R$^1$ is a butoxy group and R$^2$ is selected from the group consisting of the formulae:

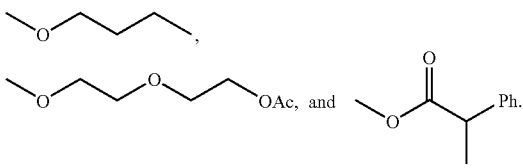

5. The compound of claim 3 wherein R$^1$ is a butoxy group; and R$^2$ is a PEGylated or biotinylated group.

6. The compound of claim 5 wherein the biotinylated group has the formula:

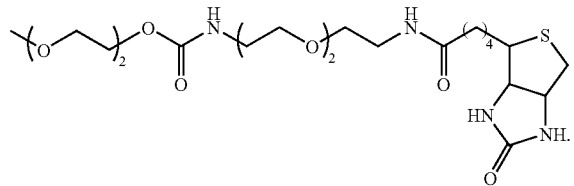

7. The compound of claim 3 wherein the dibenzocyclopropenone has the formula II:

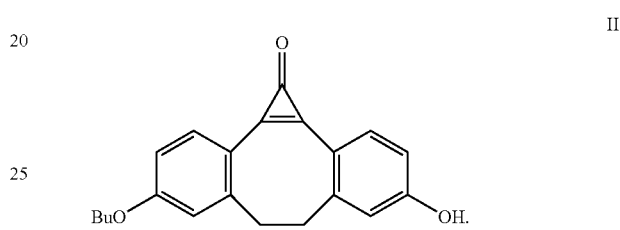

8. A method of photochemically inducing the reaction of two materials, the method comprising:
photochemically generating a cyclic alkyne from a compound according to claim 3: and
contacting the cyclic alkyne with a material comprising an alkyne-reactive group under conditions effective for the cyclic alkyne and the material comprising the alkyne-reactive group to react.

9. The method of claim 8 wherein the method photochemically induces the ligation of the cyclic alkyne and the material comprising the alkyne-reactive group.

10. The method of claim 8 wherein the method forms a cyclic adduct.

11. The method of claim 10 wherein the material comprising the alkyne-reactive group is a 1,3-dipole-functional compound.

12. The method of claim 11 wherein the cyclic adduct is a heterocyclic compound.

13. The method of claim 12 wherein the 1,3-dipole-functional compound is selected from the group consisting of azide-functional compounds, nitrile oxide-functional compounds, nitrone-functional compounds, azoxy-functional compounds, acyl diazo-functional compounds, and combinations thereof.

14. The method of claim 13 wherein the 1,3-dipole-functional compound is an azide-functional compound, and the cyclic adduct is a triazole.

15. The method of claim 10 wherein the material comprising the alkyne-reactive group is a diene, and the cyclic adduct is a Diels-Alder adduct.

16. The method of claim 10 wherein the material comprising the alkyne-reactive group is a nitrosoarene, and the cyclic adduct is an N-hydroxy indole.

17. The method of claim 10 wherein the material comprising the alkyne-reactive group is a metal-containing compound.

18. The method of claim 17 wherein the metal-containing compound is a four- or five-membered platinacycle.

19. The method of claim 10 wherein the material comprising the alkyne-reactive group is carbon monoxide, the method further comprising contacting the cyclic alkyne with an alkene, and the cyclic adduct is a [2+2+1] cycloaddition product.

20. The method of claim 8 wherein the material comprising the alkyne-reactive group is a metal carbene complex, the method further comprising contacting the cyclic alkyne with an alkene under conditions effective to form a butadiene.

21. The method of claim 20 wherein the method comprises enyne metathesis.

22. The method of claim 8 wherein the material comprising the alkyne-reactive group is an alkyne, the method further comprising contacting the cyclic alkyne with a metal catalyst under conditions effective to form a different alkyne.

23. The method of claim 22 wherein the method comprises alkyne metathesis.

24. A method of photochemically inducing the ligation of two molecules, comprising:
   (a) photochemically generating a cyclic alkyne from a compound according to claim 3; and
   (b) contacting the cyclic alkyne with an azide under conditions effective to form a triazole.

25. The method of claim 24 wherein the azide or the cyclic alkyne is bound to the surface of a substrate.

26. The method of claim 24 wherein the azide or the cyclic alkyne is integrated into a substrate layer.

27. The method of claim 25 wherein the substrate is a solid substrate or a cell membrane.

28. The method of claim 26 wherein the substrate is a cell membrane.

29. The method of claim 25 wherein, if the azide is bound to the surface of a substrate or integrated into a substrate layer, then the cyclic alkyne is a ligand that binds to the azide, and wherein if the cyclic alkyne is bound to the surface of a substrate or integrated into a substrate layer, then the azide is a ligand that binds to the cyclic alkyne.

30. The method of claim 29 wherein the azide ligand or the cyclic alkyne ligand is a detectable label.

31. The method of claim 24 wherein $R^1$ is a butoxy group and $R^2$ is selected from the group consisting of the formulae:

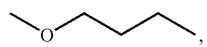

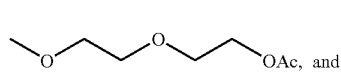 OAc, and 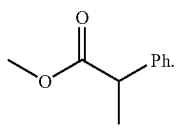

32. The method of claim 24 wherein $R^1$ is a butoxy group; and $R^2$ is a PEGylated or biotinylated group.

33. The method of claim 32 wherein the biotinylated group has the formula:

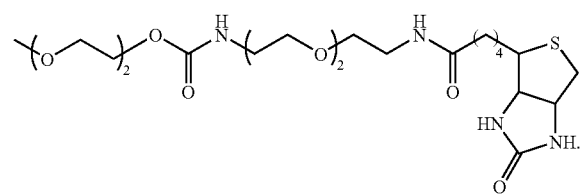

34. The method of claim 24 wherein the dibenzocyclopropenone has the formula II:

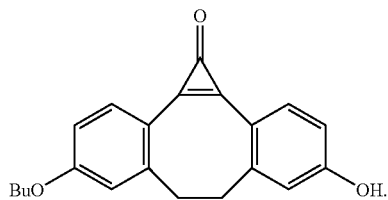

35. The method of claim 24 wherein the azide is selected from the group consisting of: an alkyl azide, a heteroalkyl azide, a cycloalkyl azide, a heterocycloalkyl azide, an alkylamino azide, a benzyl azide, an aryl azide, an alkyacyl azide, and an arylacyl azide.

36. The method of claim 24 wherein step (a) comprises irradiating the cyclopropenone with light having a wavelength selectively absorbed by the cyclopropenone, and substantially not absorbed by a cyclic alkyne or by a triazole.

37. The method of claim 36 wherein the wavelength of light is from about 220 nm to about 450 nm.

38. The method of claim 24 wherein the method further comprises the step of providing a cyclopropenone, said step comprising:
   (i) providing a 3,3'-dialkyloxybibenzyl; and
   (ii) reacting the 3,3'-dialkyloxybibenzyl with tetrachloropenone in the presence of anhydrous aluminum chloride under medium dilution conditions effective to generate a cyclopropenone.

39. The method of claim 38 wherein the 3,3'-dialkyloxybibenzyl is 3,3'-dibutoxybibenzyl, and the cyclopropenone has the formula I:

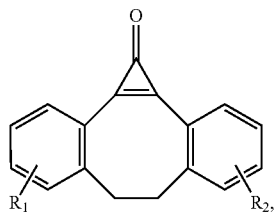

wherein $R^1$ is a butoxy group and $R^2$ is a butoxy group or a hydroxyl.

40. The method of claim 38 wherein the yield of the reaction in step (ii) comprises a compound having the formula II and a compound having the formula III:

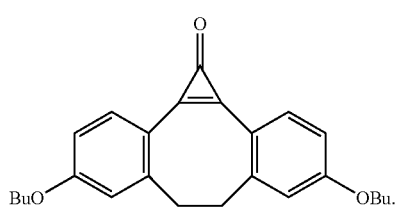

41. The method of claim 24 wherein the azide has the formula:

wherein R³ is selected from the group consisting of: an alkyl, a heteroalkyl, a cycloalkyl, a heterocycloalkyl, an alkylamino, an aryl, an alkylacyl, and an arylacyl.

42. The method of claim 24 wherein the triazole has the formula:

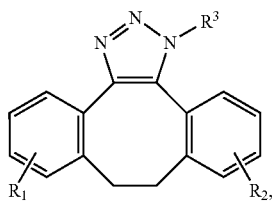

wherein:
R¹ is selected from the group consisting of: an alkoxy and a hydroxyl;
R² is selected from the group consisting of: an alkyl, a heteroalkyl, a cycloalkyl, a heterocycloalkyl, an aryl, an alkoxy, a carboxy, a hydroxyl, an ether, an ester, and a halogen; and
R³ is selected from the group consisting of a primary alkyl, a secondary alkyl, a tertiary alley, an aryl, an alkylaryl, an acyl, an alkylacyl, and an arylacyl.

43. A method of photochemically inducing the reaction of two materials, the method comprising:
photochemically generating a cyclic alkyne from a compound according to claim 1; and
contacting the cyclic alkyne with a material comprising an alkyne-reactive group under conditions effective for the cyclic alkyne and the material comprising the alkyne-reactive group to react.

44. A method of photochemically inducing the reaction of two materials, the method comprising:
photochemically generating a cyclic alkyne from a compound according to claim 2; and
contacting the cyclic alkyne with a material comprising an alkyne-reactive group under conditions effective for the cyclic alkyne and the material comprising the alkyne-reactive group to react.

* * * * *